United States Patent
Bydlon et al.

(10) Patent No.: US 12,229,950 B2
(45) Date of Patent: Feb. 18, 2025

(54) DYNAMIC INTERVENTIONAL THREE-DIMENSIONAL MODEL DEFORMATION

(71) Applicant: KONINKLIJKE PHILIPS N.V., Eindhoven (NL)

(72) Inventors: Torre Michelle Bydlon, Melrose, MA (US); Paul Thienphrapa, Cambridge, MA (US); Alvin Chen, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 664 days.

(21) Appl. No.: 17/438,990

(22) PCT Filed: Mar. 13, 2020

(86) PCT No.: PCT/EP2020/056902
§ 371 (c)(1),
(2) Date: Sep. 14, 2021

(87) PCT Pub. No.: WO2020/182997
PCT Pub. Date: Sep. 17, 2020

(65) Prior Publication Data
US 2022/0156925 A1 May 19, 2022

Related U.S. Application Data
(60) Provisional application No. 62/818,622, filed on Mar. 14, 2019.

(51) Int. Cl.
*G06T 7/12* (2017.01)
*A61B 34/20* (2016.01)
(Continued)

(52) U.S. Cl.
CPC ............ *G06T 7/0012* (2013.01); *A61B 34/20* (2016.02); *G06T 7/149* (2017.01); *G06T 15/08* (2013.01);
(Continued)

(58) Field of Classification Search
CPC ....... G06T 7/0012; G06T 7/149; G06T 15/08; G06T 2207/10121; G06T 2207/30061; A61B 34/20; A61B 2034/2065
(Continued)

(56) References Cited

U.S. PATENT DOCUMENTS 9,265,468 B2  2/2016 Gibbs
2005/0182295 A1  8/2005 Glenny
(Continued)

OTHER PUBLICATIONS

International Search Report for PCT/EP2020/056902 dated Mar. 13, 2020.

*Primary Examiner* — Michael R Neff

(57) ABSTRACT

A controller for assisting navigation in an interventional procedure includes a memory that stores instructions and a processor (310) that executes the instructions. When executed by the processor (310), the instructions cause the controller to implement a process that includes obtaining (S410) a three-dimensional model generated prior to an interventional procedure based on segmenting pathways with a plurality of branches in a subject of the interventional procedure. The process also includes determining (S470), during the interventional procedure, whether a current position of a tracked device (250) is outside of the pathways in the three-dimensional model. When the current position of the tracked device (250) is outside of the pathways in the three-dimensional model, the process includes deforming (S480) the three-dimensional model to the current position of the tracked device (250).

13 Claims, 10 Drawing Sheets

(51) Int. Cl.
  *G06T 7/00* (2017.01)
  *G06T 7/149* (2017.01)
  *G06T 15/08* (2011.01)

(52) U.S. Cl.
  CPC ............... *A61B 2034/2065* (2016.02); *G06T 2207/10121* (2013.01); *G06T 2207/30061* (2013.01)

(58) Field of Classification Search
  USPC ........................................................ 382/128
  See application file for complete search history.

(56) References Cited

U.S. PATENT DOCUMENTS

| | | |
|---|---|---|
| 2012/0059248 A1 | 3/2012 | Holsing |
| 2013/0303893 A1 | 11/2013 | Duindam |
| 2014/0039306 A1* | 2/2014 | Klinder ............... A61B 6/032 600/424 |
| 2016/0005220 A1 | 1/2016 | Barak |
| 2016/0302869 A1* | 10/2016 | Chopra ............... A61B 34/30 |
| 2016/0331343 A1 | 11/2016 | Holsing |
| 2018/0085169 A1 | 3/2018 | Krimsky |
| 2018/0235709 A1 | 8/2018 | Donhowe |
| 2018/0338799 A1 | 11/2018 | Hladio |

\* cited by examiner

DYNAMIC INTERVENTIONAL THREE-DIMENSIONAL MODEL DEFORMATION

CROSS-REFERENCE TO PRIOR APPLICATIONS

This application is the U.S. National Phase application under 35 U.S.C. § 371 of International Application No. PCT/EP2020/056902 filed on Mar. 13, 2020, which claims the benefit of U.S. Provisional Patent Application No. 62/818,622, filed on Mar. 14, 2019. These applications are hereby incorporated by reference herein.

BACKGROUND

Optical shape sensing (OSS) can be used to determine the shape of an optical fiber by using light along the optical fiber. The optical fiber can be provided in or on an interventional medical device to determine the shape of the interventional medical device. Information of the shape of the optical fiber can be used for localizing and navigating the interventional medical device during surgical intervention. Optical shape sensing is based on the principle that the wavelengths of reflected light differ under distinct circumstances. Distributed strain measurements in the optical fiber can therefore be used to determine the shape of the optical fiber using characteristic Rayleigh backscatter or controlled grating patterns.

Examples of interventional medical devices include guidewires, catheters, sheaths, and bronchoscopes, and optical shape sensing can be used to provide live positions and orientations of such interventional medical devices for guidance during minimally invasive procedures.

One example of using optical shape sensing with an interventional device is to embed the optical fiber in a guidewire and navigate the guidewire through a channel in the body of the interventional device. FIG. 1A illustrates a virtual image of an optical fiber 101 embedded in a guidewire 102. The three-dimensional position of the guidewire 102 can then be registered to anatomical imaging modalities, such as x-ray or computed tomography (CT), to provide the anatomical context of the guidewire 102 and a shape sensed interventional device (e.g., a bronchoscope) to which the guidewire 102 is inserted or attached.

Separate from the above, a lung lesion can be biopsied using an endobronchial approach in which a bronchoscope is guided down the airways. A camera at the end of the bronchoscope provides imagery of the airways, and an abnormal part of the airway can be biopsied using a small tool that is inserted via the working channel of the bronchoscope. Approaches for lung biopsy face challenges including:

the bronchoscope can only fit in large upper airways
  many lesions are not connected to any airway, large or small, and many others are in or connected to only a small airway which interventional tools cannot reach
  respiratory and cardiac motion results in large deformations in the lung The endobronchial approach may be limited to lesions that are in or connected to the upper airways since only the upper airways can fit the bronchoscope. Otherwise, visualization may be lost resulting in interventional medical devices being blindly navigated within or outside of the airways to take random tissue samples. Additionally, when the lesion is not connected to an airway the interventional medical device must puncture the airway wall and travel outside of the airway through the lung parenchyma to perform a transbronchial biopsy. A transbronchial biopsy may also be performed when the closest airway to the lesion is too small to navigate a tool.

Several methods have evolved to address these endobronchial challenges and provide better navigation to physicians. In some of these methods, a pre-operative three-dimensional image of the lung is acquired and processed with algorithms to produce a three-dimensional model of the airways and lesion. Then, the physician can navigate using this three-dimensional model, with or without x-ray and/or a bronchoscope. However, three-dimensional models are limited to what the airways look like at the time of the pre-operative imaging. In addition to the imaging, some navigation methods also use tracking technology, like electromagnetic navigation, which tracks the three-dimensional position of certain locations of the interventional devices. However, other than optical shape sensing, most tracking techniques rely on locating the tip of the interventional medical device, and this is problematic due to respiratory and cardiac motion.

In addition to the challenges with lung biopsies described above, three major challenges are encountered in lung tumor surgery, regardless of the type of lung tumor surgery being performed. The location of the tumor may be initially determined based on a pre-operative computed tomography (CT) scan performed with the lung inflated. During surgery the lung is collapsed and therefore the three-dimensional orientation of the lung, and location of the tumor, do not match the pre-operative images which are used for planning. FIG. 1B illustrates a comparison between an inflated view of a lung and a collapsed view of the lung. This is further complicated by the fact that the lung is typically moved and re-positioned throughout the surgical procedure. This motion can cause the surgeon to lose track of the tumor location with respect to the surface of the lung and orientation of the lobes. Second, the lung is very complex with many blood vessels and airways which have to be carefully dissected and dealt with before the tumor and any feeding airways or vessels are removed. Third, small, non-palpable tumors are very hard to locate in the lung, especially with video-assisted thoracoscopic surgery (VATS) or robotic surgery.

FIG. 1C illustrates a three-dimensional model of the airways and tumor with a planned path to reach the tumor. FIG. 1C also shows an overlaying of a planned path for an interventional procedure onto real-time fluoroscopy images of airways and a tumor. The planned path 103 from the trachea is shown as a thin line from the top. The current position 106 of the bronchoscope is also seen in the fluoroscopy image to the right of the planned path 103. The tumor location 104 is shown at the end of the planned path 103. However, the three-dimensional model in FIG. 1C is static. Therefore, there is no way provided to adjust the three-dimensional model.

As described herein, dynamic interventional three-dimensional model deformation can be used to enhance localization and navigation for interventional medical devices.

SUMMARY

According to a representative embodiment of the present disclosure, a controller for assisting navigation in an interventional procedure includes a memory that stores instructions and a processor that executes the instructions. When executed by the processor, the instructions cause the controller to implement a process. The process includes obtaining a three-dimensional model generated prior to an interventional procedure based on segmenting pathways with a plurality of branches in a subject of the interventional procedure. The process also includes determining, during the interventional procedure, whether a current position of a tracked device is outside of the pathways in the three-dimensional model. When the current position of the tracked device is outside of the pathways in the three-dimensional model, the process includes deforming the three-dimensional model to the current position of the tracked device.

According to another representative embodiment of the present disclosure, a method for assisting navigation in an interventional procedure includes obtaining a three-dimensional model generated prior to an interventional procedure based on segmenting pathways with a plurality of branches in a subject of the interventional procedure. The method also includes determining, during the interventional procedure by a controller executing instructions with a processor, whether a current position of a tracked device is outside of the pathways in the three-dimensional model. When the current position of the tracked device is outside of the pathways in the three-dimensional model, the method also includes deforming the three-dimensional model to the current position of the tracked device.

According to yet another representative embodiment, a system for assisting navigation in an interventional procedure includes an imaging apparatus and a computer. The imaging apparatus generates, prior to an interventional procedure, computed tomography images of a subject of an interventional procedure to be used in generating, prior to the interventional procedure, a three-dimensional model based on segmenting pathways with a plurality of branches in the subject of the interventional procedure. The computer includes a memory that stores instructions and a processor that executes the instructions. When executed by the processor, the instructions cause the system to execute a process that includes obtaining the three-dimensional model generated prior to the interventional procedure. The process executed when the process executes instructions also includes determining whether a current position of a tracked device is outside of the pathways in the three-dimensional model. When the current position of the tracked device is outside of the pathways in the three-dimensional model, the process includes deforming the three-dimensional model to the current position of the tracked device.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
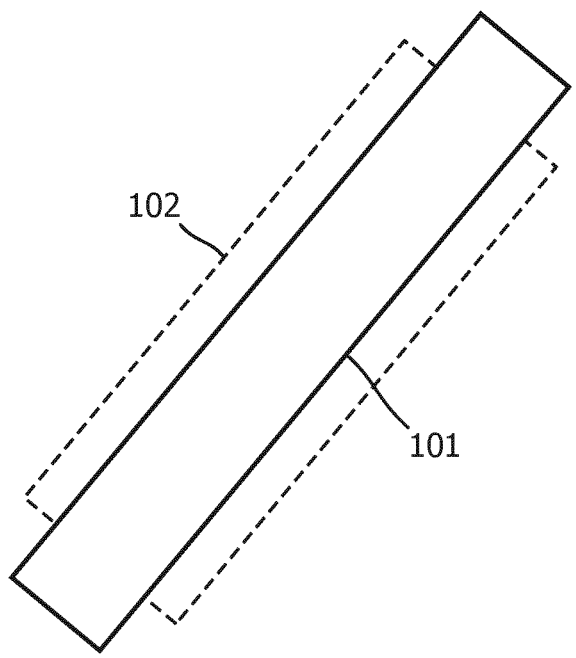
FIG. 1A illustrates a virtual image of an optical fiber inserted in the working channel of a broncho scope.
Figure 1B:
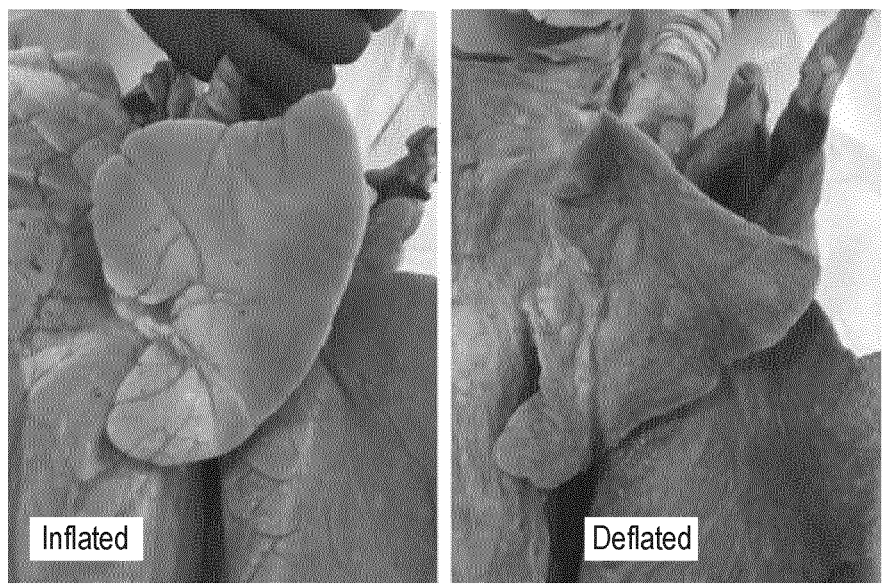
FIG. 1B illustrates a comparison between an inflated view of a lung and a collapsed view of the lung.
Figure 1C:
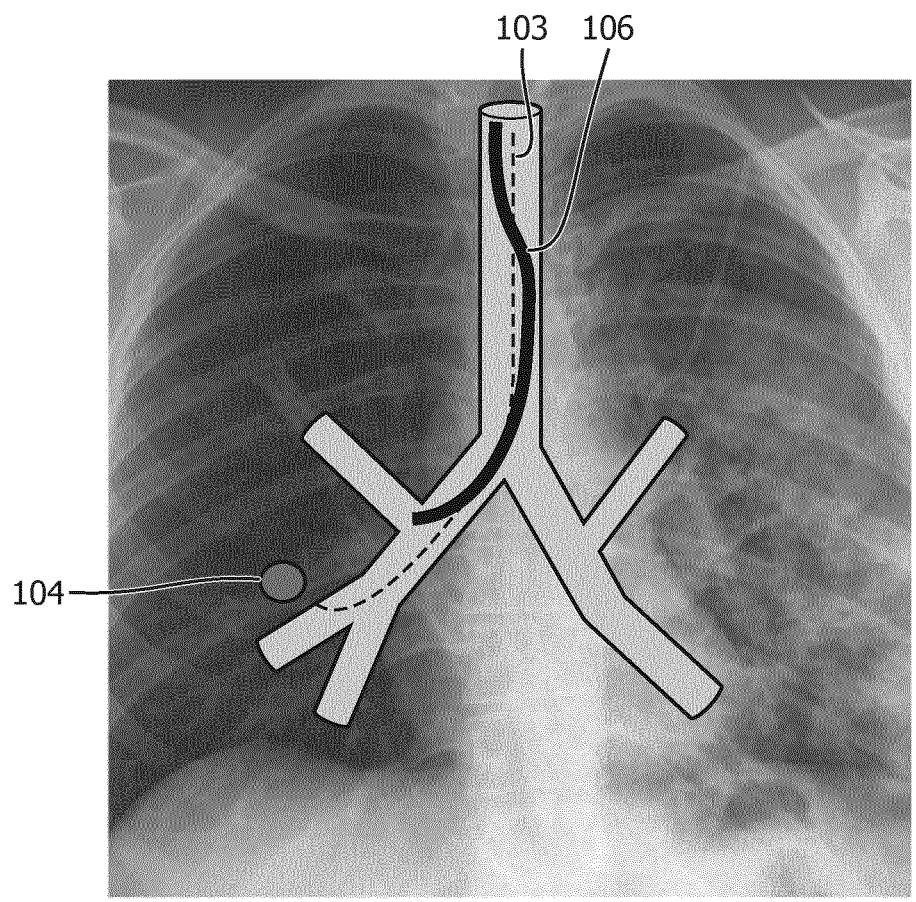
FIG. 1C illustrates a three-dimensional model of the airways and tumor with a planned path to reach the tumor. It also shows an overlay of real-time fluoroscopy images of the anatomy during an interventional procedure, including the position of an interventional device inside the airways.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Figure 2:
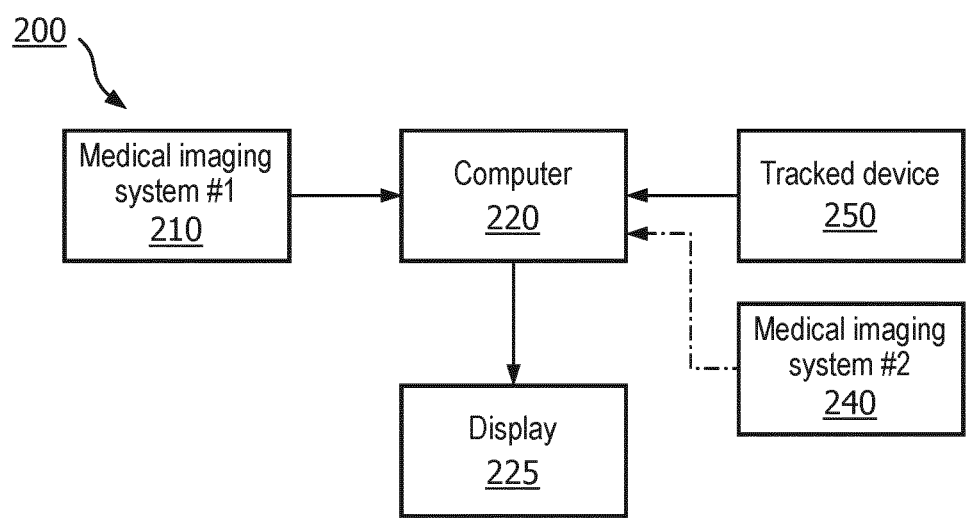
FIG. 2 illustrates a system for dynamic interventional three-dimensional model deformation, in accordance with a representative embodiment.

FIG. 2 illustrates a system for dynamic interventional three-dimensional model deformation, in accordance with a representative embodiment.

The system 200 of FIG. 2 includes a first medical imaging system 210, a computer 220, a display 225, a second medical imaging system 240 and a tracked device 250. The system in FIG. 2 may be used for dynamic interventional three-dimensional model deformation, such as for medical interventions to repair, replace or adjust an organ such as a lung, or to otherwise intervene in the body of a subject.

An example of the first medical imaging system 210 is an X-ray system that includes an X-ray machine. The first medical imaging system 210 may perform computed tomography scanning or cone based computed tomography scanning prior to a medical intervention that involves the three-dimensional model deformation described herein. The three-dimensional model may be generated before or during the medical intervention based on the scanning by the first medical imaging system 210. Additionally, while the medical imaging by the first medical imaging system 210 may be performed prior to the medical intervention, this medical imaging may also be performed during the medical intervention.

The tracked device 250 may be tracked using optical shape sensing or any other tracking technology like sensor-based electromagnetism. The tracked device 250 sends positional information to the computer 220. The computer 220 processes the medical images from the first medical imaging system 210 to generate the three-dimensional model. The computer 220 also processes data from the tracked device 250 to perform the deformation and adjustments to the three-dimensional model.

An example of the second medical imaging system 240 is an ultrasound apparatus used to obtain ultrasound images during a medical intervention that involves the three-dimensional model deformation described herein. Another example of the second medical imaging system 240 is another X-ray system that includes an X-ray machine used to obtain fluoroscopic images during a medical intervention that involves the three-dimensional model deformation described herein. The second medical imaging system 240 may be used to track a medical device that is otherwise untracked such that the medical device becomes the tracked device 250. For example, some medical devices do not have optical shape sensing or electromagnetic tracking components disposed therein or thereon. Locating such a medical device in the x-ray image or using anatomical information from the ultrasound images provides the positional information of the otherwise un-tracked medical device such that it becomes the tracked device 250. Of course, a medical device may be a tracked device 250 with both a tracking technology embedded therein or thereon (e.g., optical shape sensing), while also being tracked simultaneously with the medical imaging modality of the second medical imaging system 240.

Additionally, the first medical imaging system 210 and the second medical imaging system 240 may both be present and used during the medical intervention, such as when the first medical imaging system 210 is the X-ray system used for fluoroscopic imaging during the medical intervention and the second medical imaging system 240 is the ultrasound system used for ultrasound imaging during the medical intervention. Alternatively, only one of the first medical imaging system 210 or the second medical imaging system 240 is present and used during the medical intervention. For example, the first medical imaging system 210 may be used during a certain type of medical intervention, while the second medical imaging system 240 is only used as an additional component such as when x-ray or ultrasound is used as the tracking method.

The first medical imaging system 210 may be used to generate computed tomography images that serves as the basis for generating a three-dimensional model as described herein. The computed tomography images are an example of three-dimensional anatomical images. The second medical imaging system 240 may be used to perform imaging that is used to track a tracked device. A tracked device may refer to an interventional medical device on or in which a sensor, optical shape sensing element or other tracking element is provided. In FIG. 2, the imaging that is used to track a tracked device may be performed in real-time using the second medical imaging system 240 alone or using both the second medical imaging system 240 and the first medical imaging system 210. In other words, the second medical imaging system 240 may be present and used during the interventional procedure without the first medical imaging system 210 or with the first medical imaging system 210. The second medical imaging system 240 provides imaging data to the computer 220.

In FIG. 2, the computer 220 includes a display 225. The display may be used to display the three-dimensional model based on the imaging performed by the first medical imaging system 210, along with imagery obtained during a medical intervention based on the imaging performed by the second medical imaging system 240. Imagery obtained during a medical intervention may be, for example, imagery of an inflated lung that is deflated during the medical intervention. As the term "display" is used herein, the term should be interpreted to include a class of features such as a "display device" or "display unit", and these terms encompass an output device, or a user interface adapted for displaying images and/or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Any of the elements in FIG. 2 may include a controller described herein. A controller described herein may include a combination of a memory that stores instructions and a processor that executes the instructions in order to implement processes described herein. A controller may be housed within or linked to a workstation such as the computer 220 or another assembly of one or more computing devices, a display/monitor, and one or more input devices (e.g., a keyboard, joysticks and mouse) in the form of a standalone computing system, a client computer of a server system, a desktop or a tablet. The descriptive label for the term "controller" herein facilitates a distinction between controllers as described herein without specifying or implying any additional limitation to the term "controller". The term "controller" broadly encompasses all structural configurations, as understood in the art of the present disclosure and as exemplarily described in the present disclosure, of an application specific main board or an application specific integrated circuit for controlling an application of various principles as described in the present disclosure. The structural configuration of the controller may include, but is not limited to, processor(s), computer-usable/computer readable storage medium(s), an operating system, application module(s), peripheral device controller(s), slot(s) and port(s).

Additionally, although FIG. 2 shows components networked together, two such components may be integrated into a single system. For example, the computer 220 may be integrated with the first medical imaging system 210. That is, in embodiments, functionality attributed to the computer 220 may be implemented by (e.g., performed by) a system that includes the first medical imaging system 210. On the other hand, the networked components shown in FIG. 2 may also be spatially distributed such as by being distributed in different rooms or different buildings, in which case the networked components may be connected via data connections. In still another embodiment, one or more of the components in FIG. 2 is not connected to the other components via a data connection, and instead is provided with input or output manually such as by a memory stick or other form of memory. In yet another embodiment, functionality described herein may be performed based on functionality of the elements in FIG. 2 but outside of the system shown in FIG. 2.

Any of the first medical imaging system 210, the computer 220, and the second medical imaging system 240 in FIG. 2 may include some or all elements and functionality of the general computer system described below with respect to FIG. 3. For example, the computer 220 may include a controller for determining whether a current position of a tracked device is outside of the pathways in a three-dimensional model. A process executed by a controller may include receiving a three-dimensional model of pathways with multiple branches in a subject of an interventional procedure or receiving image data and generating based on the image data the three-dimensional model of pathways with the multiple branches in the subject of the interventional procedure.

The process implemented when a controller of the computer 220 executes instructions also includes determining whether a current position of a tracked device is outside of the pathways in the three-dimensional model, and when the current position of the tracked device is outside of the pathways in the three-dimensional model, deforming the three-dimensional model to the current position of the tracked device. The same controller may also execute the functionality of generating a three-dimensional model based on segmenting pathways with a plurality of branches in a subject of an interventional procedure. However, the controller that tracks positions of the tracked device may obtain a segmented three-dimensional model that is generated and segmented elsewhere, such as by the first medical imaging system 210 or by the computer 220 executing instructions to process medical imagery created by the first medical imaging system 210. That is, a process implemented by a controller as described herein may include obtaining a three-dimensional model generated prior to an interventional procedure, wherein the three-dimensional model was generated based on segmenting pathways with a plurality of branches in a subject of the interventional procedure. The three-dimensional model does not, however, have to be generated "prior to" the interventional procedure. For example, in some embodiments the models are generated or updated during the interventional procedure and then the subsequent processes are still performed. As noted above, even the medical imaging by the first medical imaging system 210 may be performed during the same medical intervention in which the interventional three-dimensional model deformation is performed.

Figure 3:
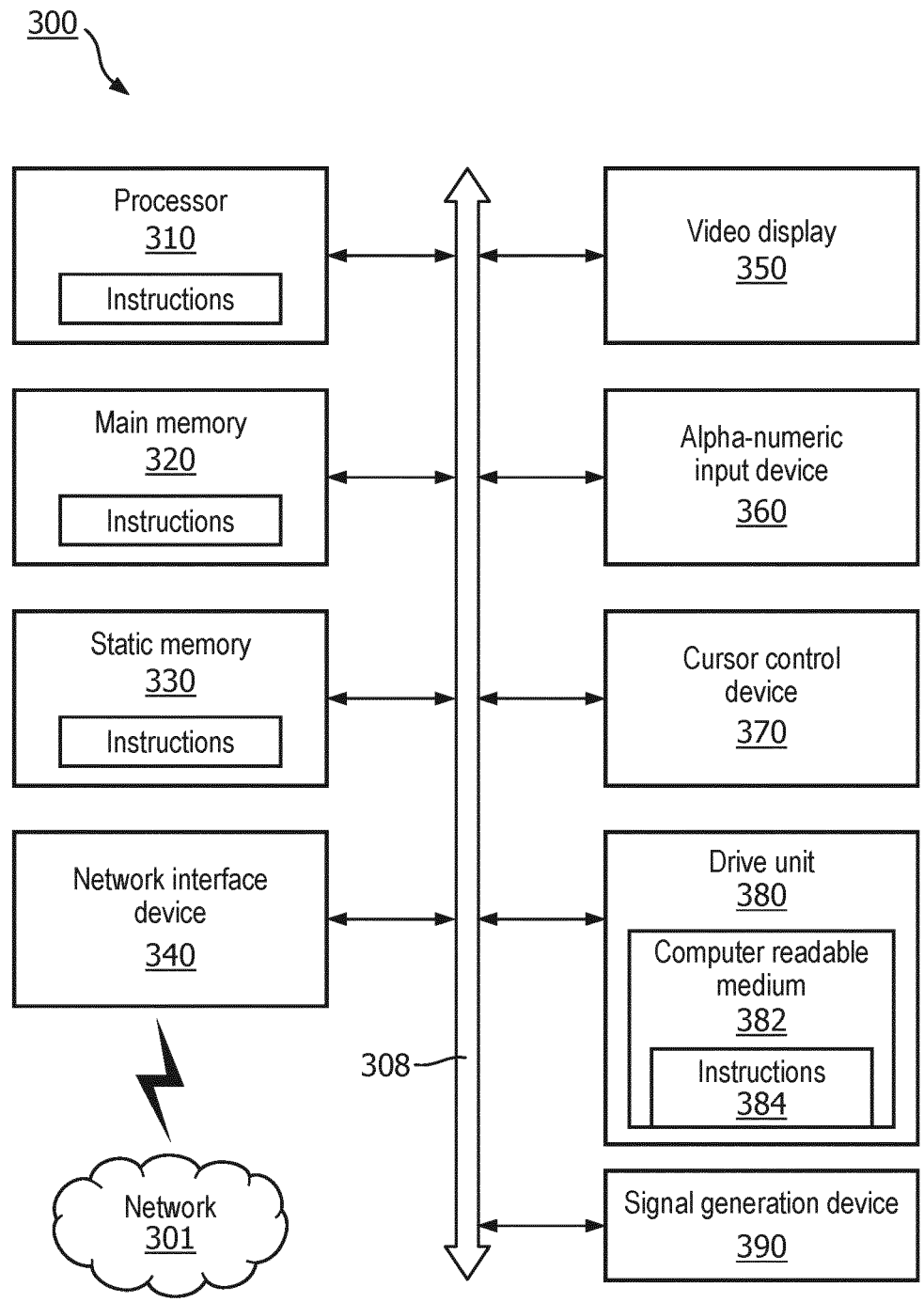
FIG. 3 illustrates a general computer system, on which a method of dynamic interventional three-dimensional model deformation can be implemented, in accordance with another representative embodiment.

FIG. 3 illustrates a general computer system, on which a method of dynamic interventional three-dimensional model deformation can be implemented, in accordance with another representative embodiment.

The computer system 300 can include a set of instructions that can be executed to cause the computer system 300 to perform any one or more of the methods or computer-based functions disclosed herein. The computer system 300 may operate as a standalone device or may be connected, for example, using a network 301, to other computer systems or peripheral devices.

In a networked deployment, the computer system 300 may operate in the capacity of a server or as a client user computer in a server-client user network environment, or as a peer computer system in a peer-to-peer (or distributed) network environment. The computer system 300 can also be implemented as or incorporated into various devices, such as the first medical imaging system 210, the computer 220, the second medical imaging system 240, a stationary computer, a mobile computer, a personal computer (PC), a laptop computer, a tablet computer, or any other machine capable of executing a set of instructions (sequential or otherwise) that specify actions to be taken by that machine. The computer system 300 can be incorporated as or in a device that in turn is in an integrated system that includes additional devices. In an embodiment, the computer system 300 can be implemented using electronic devices that provide voice, video or data communication. Further, while the computer system 300 is illustrated in the singular, the term "system" shall also be taken to include any collection of systems or sub-systems that individually or jointly execute a set, or multiple sets, of instructions to perform one or more computer functions.

As illustrated in FIG. 3, the computer system 300 includes a processor 310. A processor for a computer system 300 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor for a computer system 300 is configured to execute software instructions to perform functions as described in the various embodiments herein. A processor for a computer system 300 may be a general-purpose processor or may be part of an application specific integrated circuit (ASIC). A processor for a computer system 300 may also be a microprocessor, a microcomputer, a processor chip, a controller, a microcontroller, a digital signal processor (DSP), a state machine, or a programmable logic device. A processor for a computer system 300 may also be a logical circuit, including a programmable gate array (PGA) such as a field programmable gate array (FPGA), or another type of circuit that includes discrete gate and/or transistor logic. A processor for a computer system 300 may be a central processing unit (CPU), a graphics processing unit (GPU), or both. Additionally, any processor described herein may include multiple processors, parallel processors, or both. Multiple processors may be included in, or coupled to, a single device or multiple devices.

A "processor" as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each including a processor or processors. Many programs have instructions performed by multiple processors that may be within the same computing device or which may even be distributed across multiple computing devices.

Moreover, the computer system 300 may include a main memory 320 and a static memory 330, where memories may can communicate with each other via a bus 308. Memories described herein are tangible storage mediums that can store data and executable instructions and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 300 may further include a video display unit 350, such as a liquid crystal display (LCD), an organic light emitting diode (OLED), a flat panel display, a solid-state display, or a cathode ray tube (CRT). Additionally, the computer system 300 may include an input device 360, such as a keyboard/virtual keyboard or touch-sensitive input screen or speech input with speech recognition, and a cursor control device 370, such as a mouse or touch-sensitive input screen or pad. The computer system 300 can also include a disk drive unit 380, a signal generation device 390, such as a speaker or remote control, and a network interface device 340.

In an embodiment, as depicted in FIG. 3, the disk drive unit 380 may include a computer-readable medium 382 in which one or more sets of instructions 384, e.g. software, can be embedded. Sets of instructions 384 can be read from the computer-readable medium 382. Further, the instructions 384, when executed by a processor, can be used to perform one or more of the methods and processes as described herein. In an embodiment, the instructions 384 may reside completely, or at least partially, within the main memory 320, the static memory 330, and/or within the processor 310 during execution by the computer system 300.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionalities as described herein, and a processor described herein may be used to support a virtual processing environment.

The present disclosure contemplates a computer-readable medium 382 that includes instructions 384 or receives and executes instructions 384 responsive to a propagated signal; so that a device connected to a network 301 can communicate voice, video or data over the network 301. Further, the instructions 384 may be transmitted or received over the network 301 via the network interface device 340.

Figure 4:
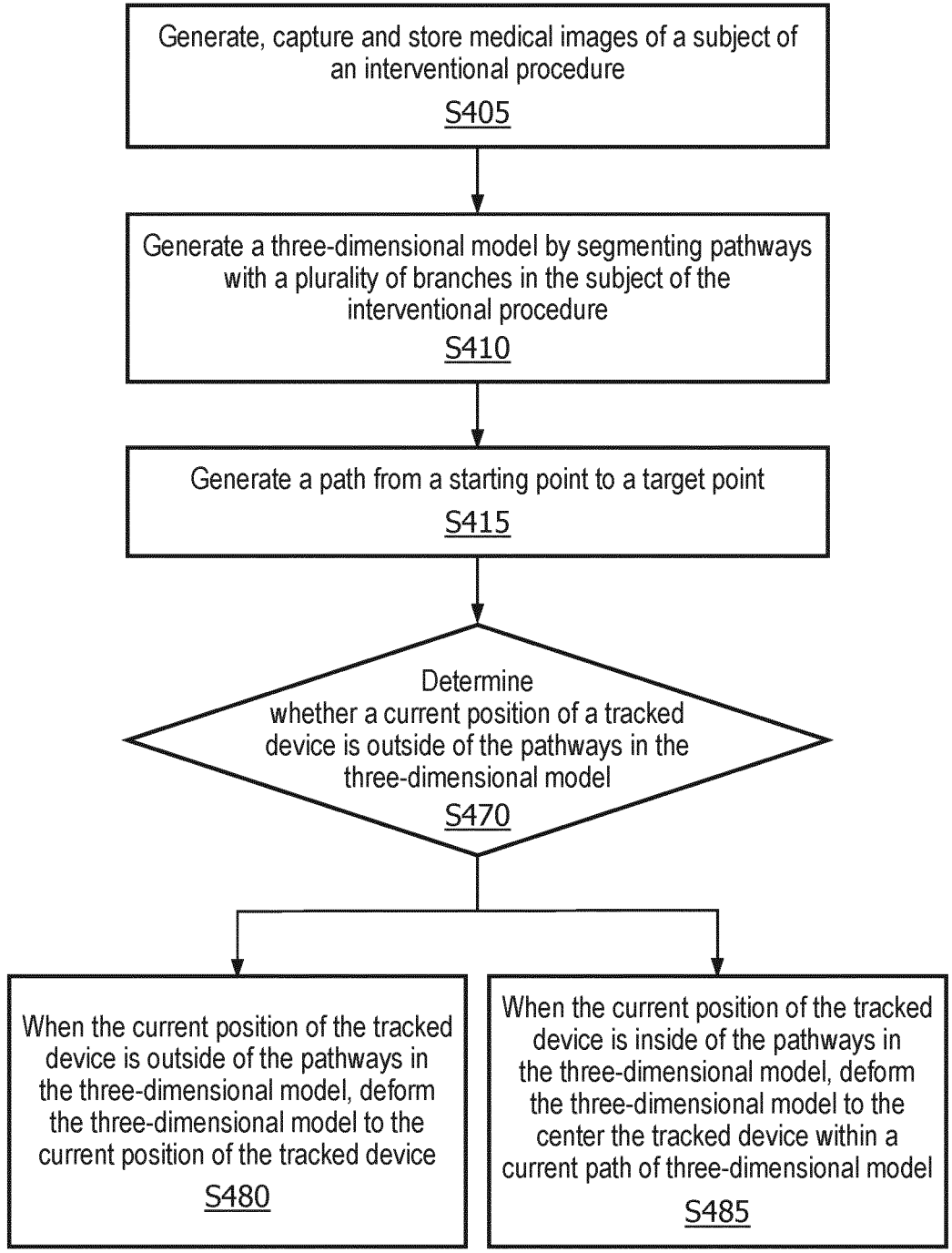
FIG. 4 illustrates a method of dynamic interventional three-dimensional model deformation, in accordance with a representative embodiment.

FIG. 4 illustrates a method of dynamic interventional three-dimensional model deformation, in accordance with a representative embodiment.

The method in FIG. 4 starts at S405 by generating, capturing and storing medical images of a subject of an interventional procedure. In some embodiments of dynamic interventional three-dimensional model deformation, pre-operative computed tomography (CT) or cone-beam computed tomography (cone-beam computed tomography) images of the airways are acquired. Cone-beam computed tomography is a medical imaging technique that involves X-ray computed tomography where the X-rays are divergent and resultingly form a cone. The airways are segmented as described herein in most embodiments. The computed tomography or cone-beam computed tomography imaging and segmenting may be performed prior to an interventional operation in most embodiments. Three-dimensional images may be acquired using computed tomography, cone-beam computed tomography, magnetic resonance, or other imaging modalities that provide a three-dimensional representation of anatomy.

At S410, the method in FIG. 4 includes generating a three-dimensional model based on segmenting pathways with multiple (a plurality of) branches in the subject of the interventional procedure. The three-dimensional model of the pathways may be generated based on the cone-beam computed tomography, or any other three-dimensional imaging modality. The three-dimensional model is of airways in the example of lungs but may be blood vessels in alternative embodiments. Additionally, while S410 specifies that the three-dimensional model is created by segmenting, a three-dimensional model may also be created by other mechanisms such as rendering. Segmentation is a representation of the surface of structures such as the pathways and branches of lungs or the components of a heart and consists for example of a set of points in three-dimensional (3-D) coordinates on the surface of the organ, and triangular plane segments defined by connecting neighboring groups of 3 points, such that the entire structure is covered by a mesh of non-intersecting triangular planes.

At S415, the method in FIG. 4 includes generating a path from a starting point to a target point in the three-dimensional model.

As specified for embodiments described later, a tracked device may be registered to the three-dimensional model. Registration involves placing different elements or systems onto a common coordinate system. For example, the shape of a tracked interventional lung medical device can be registered to pre-operative lung images, which then leads to an ability to account for breathing motion, dislocation of anatomy based on interaction with the tracked interventional medical device (e.g., lung deformation), and other movement, as well as an ability to plan a lung navigation in the airways. Shape sensing can be used for real-time guidance in the presence of respiratory/cardiac motion using error deviation of the current path from the planned path to help the user time the navigation inside and outside (off-road) of the airways.

At S470, the method in FIG. 4 includes determining whether a current position of a tracked device is outside of the pathways in the three-dimensional model. In FIG. 4, tracked devices are tracked in three dimensions as the tracked devices are navigated in the airways. The tracking may be performed using optical shape sensing, but in other embodiments the tracking may involve electromagnetic sensors, ultrasound-based sensors, or x-ray-based device recognition based on dynamic analysis of fluoroscopy images. In methods described herein, optical shape sensing is generally described. However, tracked devices described herein can alternatively be tracked with electromagnetic sensors, ultrasound-based sensors, or X-ray-based device recognition from fluoroscopy images, etc.

At S480, the method in FIG. 4 includes deforming the three-dimensional model to the current position of the tracked device when the current position of the tracked device is outside of the pathways in the three-dimensional model. The deformation at S480 results in adjusting visualizations seen by a physician using a pre-operative three-dimensional model of the airways and real-time interventional medical device positions. The deforming at S480 thus results from the tracking insofar as the current path of the tracked device may be compared to the airway lumen (open space), and if the current path is outside of the closest airways, the computed tomography/cone-beam computed tomography images and the three-dimensional model are deformed.

At S485, the method in FIG. 4 includes deforming the three-dimensional model to center the tracked device within a current path of the three-dimensional model when the current position of the tracked device is inside of the pathways. As an alternative to S485, the method may include not deforming the three-dimensional model at all when the current position of the tracked device is inside of the pathways.

The method in FIG. 4 provides a physician an ability to locate an interventional medical devices with respect to the actual anatomy. In anatomical segmentations resulting in a three-dimensional model, the three-dimensional model may be based on the image acquisition as at S405. The physician using this three-dimensional model for real-time guidance can obtain information that is otherwise missing about how the anatomy is changing in real-time. For example, the airways can stretch or contract by several centimeters throughout one respiratory cycle and will shift when a stiff device like a bronchoscope is inserted. The tracking of interventional medical devices allows real-time information about the position to be used to update the three-dimensional model from its pre-operative state.

The individual steps of the method in FIG. 4 are shown in a particular order that generally will hold true for embodiments described herein. However, other steps for methods described herein may be performed in different orders than shown or may be performed on an ongoing basis concurrent with one another.

Additionally, the numbering of steps in FIG. 4 may partially or fully hold true for other embodiments described herein. For example, the numbering of S680 in FIG. 6 may be taken to mean that the step at S680 can be performed in place of S480 in FIG. 4. Similarly, the numbering of S660 in FIG. 6 may be taken to mean that the step can be performed before S470 but after S415 relative to the functionality described for FIG. 4. Thus, the relative values of the last two numerals for steps described herein for various embodiments may be taken as a general or specific placement relative to the numbering of steps in FIG. 4.

Figure 5A:
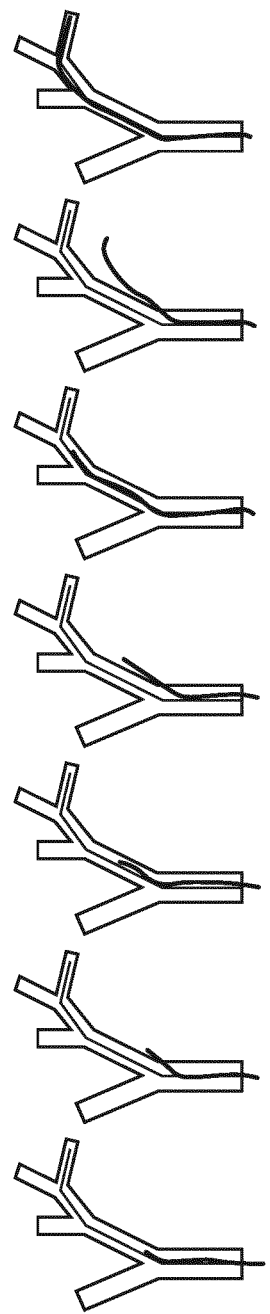
FIG. 5A illustrates comparative views of a tracked device and a three-dimensional model of pathways with multiple branches before dynamic interventional three-dimensional model deformation is applied, in accordance with a representative embodiment.

FIG. 5A illustrates comparative views of a tracked device and a three-dimensional model of pathways with multiple branches before dynamic interventional three-dimensional model deformation is applied, in accordance with a representative embodiment.

In FIG. 5A, the three-dimensional models of the pathway structure(s) are based on the point in time at which the computed tomography imagery was acquired prior to segmentation used to generate the three-dimensional model based on the image. FIG. 5A illustrates how a tracked interventional medical device can diverge from the three-dimensional models as the anatomy changes in real-time. This is illustrated in image #2, image #4 and image #6 in FIG. 5A. Therefore, if a physician is using the underlying three-dimensional model for real-time guidance, the physician is missing information about how the anatomy is changing in real-time. For example, the airways can stretch or contract several centimeters throughout one respiratory cycle and will shift when a stiff device like a bronchoscope is inserted. FIG. 5A shows visually how the interventional medical device will appear with respect to a pre-operatively acquired model. Tracked interventional medical devices allow real-time information about the position and are used herein to update what the three-dimensional pre-operative model looks like to the physician. This may be especially useful when intra-operative fluoroscopy is not being used.

In FIG. 5A, the tracked device is navigated down an airway. In image #1, image #3, image #5 and image #7 the tracked device is aligned with the airway. However, in image #2, image #4 and image #6, the interventional medical device appears outside of the airway even though the tracked device is actually within the lumen of the airway. That is, in several phases of the respiratory cycle shown in FIG. 5A, the interventional medical device appears to be outside of the airway when in reality the interventional medical device is still within the lumen.

Figure 5B:
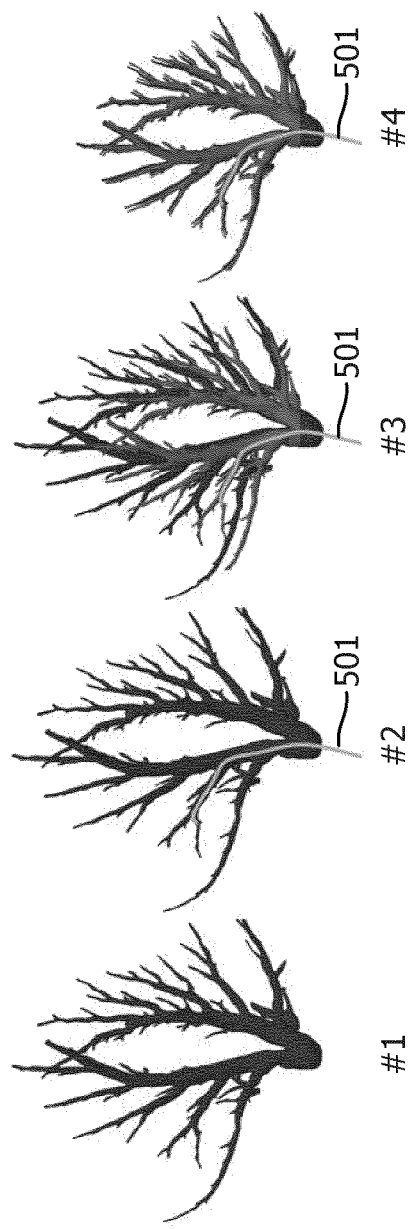
FIG. 5B illustrates a progression for dynamic interventional three-dimensional model deformation using optical shape sensing, in accordance with a representative embodiment.

FIG. 5B illustrates a progression for dynamic interventional three-dimensional model deformation using optical shape sensing, in accordance with a representative embodiment.

In FIG. 5B, a three-dimensional segmented airway is deformed using optical shape sensing feedback about respiratory motion, cardiac motion and anatomical motion due to interaction with a tracked device (e.g., lung deformation). The segmented airway shown in image #1 is a pre-operative segmented airway, where R=0 denotes that the underlying medical image is taken at one specific phase of the respiratory cycle (example, at full inspiration). For example, medical imagery underlying image #1 may be computed tomography images taken by the first medical imaging system 210 well before a medical intervention. Image #1 shows the pre-operative segmented model of the airway without a tracked interventional medical device, and image #2 shows the pre-operative segmented model of the airway with an endobronchial interventional medical device navigating the airway. In image #2, the tracking is performed using optical shape sensing as described herein. R=0 in image #2 may be taken to mean that the respiratory phase at this point in the medical intervention is at the same phase of respiration as was seen when the pre-operative image was acquired.

In FIG. 5B, at R=1 the airways move during the respiratory cycle so that the current location(s) of the airways are partly, largely or entirely offset from the original locations of the pre-operative segmented model shown in image #1. This is shown by the duplicated pathways in image #3 that are on top of and offset from the original pathways of the pre-operative segmented model carried over from image #1. That is, as shown in image #3, at time R=1 (example, full expiration of the respiratory cycle) the tracked interventional medical device and the actual pathway structure have moved away from the pre-operative segmented model shown in image #1. Accordingly, in image #4 the segmented model is deformed so that the tracked interventional medical device and the actual pathway structure fit to the actual pathway structure that exists at R=1.

As shown in image #4, deformation may involve shrinking, expanding, shifting or otherwise moving a three-dimensional model to fit the current location of a tracked device. In FIG. 5B, the position of the lungs during the respiratory phase in which the pre-operative three-dimensional scan was acquired is defined as R=0, and another phase of the respiratory cycle different from the pre-operative acquisition is defined as R=1. The three-dimensional segmented airways from R=0 are shown in each of image #1, image #2, image #3 and image #4, whereas in images #3 and images #4 the offset structure is superimposed on the three-dimensional segmented airways before and after the deforming. The offset structure represents the actual locations of the pathways at R=1. The tracked interventional medical device 501 is labelled in each of image #2, image #3 and image #4.

The example in FIG. 5B is described using tracked interventional medical devices that are tracked with optical shape sensing. However, electromagnetic sensing could alternatively be used, either with a single sensor at the tip of a tracked device or multiple sensors along the length of the tracked device. For an electromagnetic sensor at the tip, recording of the tip position could be performed continuously to track the path taken by the entire tracked device.

As described above with respect to FIG. 4, primary elements of a method described herein may involve acquiring a three-dimensional scan of the patient's airways either with pre-operative computed tomography or intra-operative cone-beam computed tomography. The pre-operative computed tomography or intra-operative cone-beam computed tomography are typically performed at one phase of the respiratory cycle. The airways and lesion are segmented from the computed tomography data to create a three-dimensional model of the airways. The resultant three-dimensional model of the airways is the starting point in image #1 in FIG. 5B. During an endobronchial lung procedure an interventional medical device can be navigated on top of the segmented model of the airway to a desired location and made to appear consistently within the airways if there is no cardiac or respiratory motion. Examples of an endobronchial lung procedure include lesion or lymph node biopsy, tumor ablation, airway stenting, tumor resection and other forms of lung procedures. If there were no cardiac or respiratory motion the interventional medical device could be navigated on top of the segmented model of the airway and the interventional medical device would always appear to stay inside the airways. However, significant motion occurs due to cardiac and respiratory motion, as well as minor movements of the patient and inserted devices. When motion occurs, the interventional medical device appears to go outside of the airways of the model and can be misleading to a physician. One benefit of optical shape sensing is that the positional information of the entire length of the interventional medical device is known at all times. This information can be used to update the model of the airway in real-time to provide a more realistic image of where the interventional medical devices are relative to the anatomy. The upper airways are very rigid, and therefore most likely the interventional medical device will be inside the lumen of the airway. However, in the peripheral (far out) airways the walls are quite thin, and the tip of an interventional medical device may easily poke outside the walls. Therefore, the deformation of the model should predominately use the information of the interventional medical device location when in the upper airways.

Figure 6:
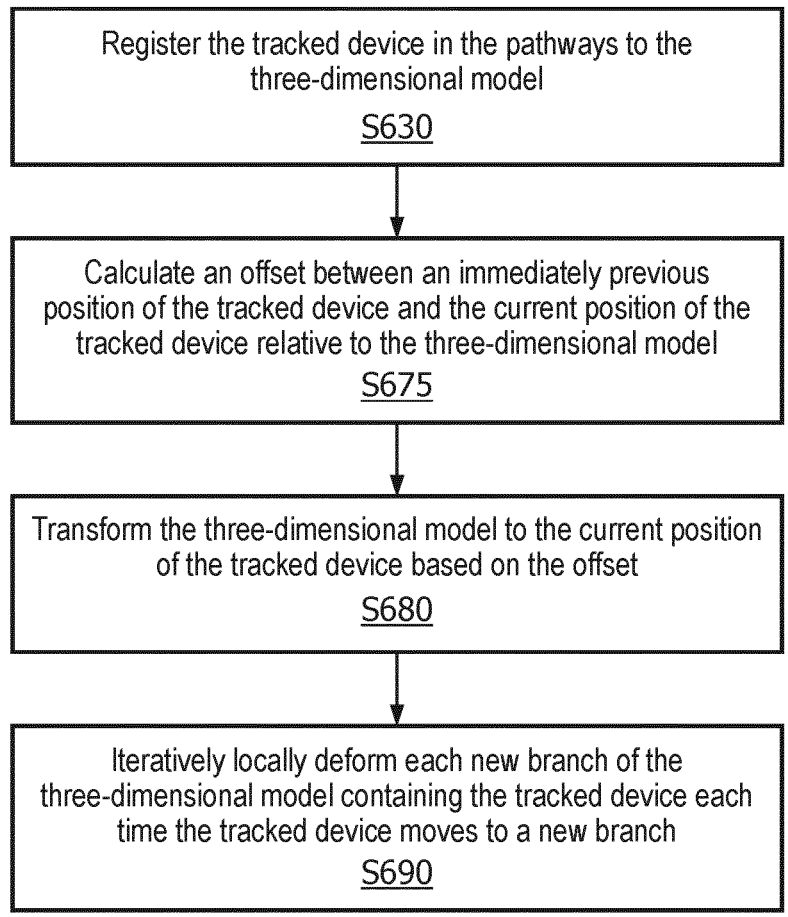
FIG. 6 illustrates another method of dynamic interventional three-dimensional model deformation, in accordance with a representative embodiment.

FIG. 6 illustrates another method of dynamic interventional three-dimensional model deformation, in accordance with a representative embodiment.

The process in FIG. 6 starts at S630 by registering the tracked device in the pathways to the three-dimensional model. Registration is a process which involves aligning different coordinate systems or assigning coordinates of an existing coordinate system to a newly introduced element. At S630, a coordinate system of the three-dimensional model may be used to assign coordinates to a tracked device so that the tracked device can be tracked in the coordinate system of the three-dimensional model. The tracked device may be tracked using optical shape sensing, and the three-dimensional model may be a pre-operative model such as in all four images in FIG. 5B.

At S675, the process in FIG. 6 includes calculating an offset between an immediately previous position of the tracked device and the current position of the tracked device relative to the three-dimensional model. Insofar as positions of the tracked device may be calculated continuously and rapidly during an interventional procedure, an offset may be used to help plot a trajectory and path for the tracked device, and also to assist in the deforming as at S480 in FIG. 4 or at S680 as described below. The calculating at S675 may be performed after a determination such as at S470 in FIG. 4 where a check is made as to whether a tracked device is inside the airway lumen of the mesh of the three-dimensional model.

At S680, the process in FIG. 6 includes transforming the three-dimensional model to the current position of the tracked device based on the offset. For example, at S680 the transformation may involve a deformation by adjusting the three-dimensional model so that the three-dimensional model includes one or more immediately previous positions of the tracked device and the current position of the tracked device.

The transforming at S680 may involve deforming the entire pre-operative three-dimensional model to the current position of the tracked device. The transforming may be based on recording the last known position of the tracked device and the current position of the tracked device and calculating the offset as at S675 insofar as recording positions assists, for example, in identifying which branches the tracked interventional medical device has already traversed. The system 200 may remember the history of the tracked device at all times and all positions, in order to facilitate the calculating at S675 and the transforming at S680.

As an alternative to S680, if the tracked device is inside the airway lumen of the mesh of the three-dimensional mode as determined at S470, the process in FIG. 6 may involve showing the pre-operative three-dimensional model in an undeformed state. Alternatively, small deformation corrections may be applied to keep the interventional medical device in the center of the lumen.

At S690, the process in FIG. 6 includes iteratively deforming each new branch of the three-dimensional model containing the tracked device each time the tracked device moves to a new branch. At S690, the location of the tracked device in each airway at each time point can be iteratively used to locally deform the airway to fit the tracked device, so as to keep the tracked device at the center of the airway lumen. The location can be identified after each deformation and each time the tracked interventional medical device is advanced further, and each time the tracked device is advanced further the local deforming may be again performed.

In the method of FIG. 6, the deformation shown in image #4 of FIG. 5B may be obtained. In FIG. 6, the tracked device may be tracked with optical shape sensing. When the tracked device is outside of the pathways, the pathways of the three-dimensional model are adjusted to the location of the tracked device. An important part of the method in FIG. 6 is that the system 200 stores the history of multiple or even all time points and positions of the tracked device as the tracked device is moved throughout the airways. These time points and positions may be critical for tracked devices where only the tip is tracked, or with minimal tracking along the length of the tracked device. The history of positions can be used to deform the three-dimensional model along the entire device trajectory and not just at the tip of the tracked device.

In the embodiment of FIG. 6, the method may be performed while navigating an optical shape sensing device in the manner shown in image #2, image #3 and image #4 of FIG. 5B. The optical shape sensing device is registered to the pre-operative three-dimensional model. Upon checking if the optical shape sensing device is inside the airway lumen/model mesh, if yes then the pre-operative three-dimensional model is shown in an undeformed state or alternatively only small deformable corrections are applied to keep the tracked device in the center of the lumen. On the other hand, if the optical shape sensing device is not inside the airway lumen/model mesh, the pre-operative three-dimensional model is deformed to the current position of the optical shape sensing device. Since positions of the optical shape sensing device are recorded on an ongoing basis, the offset between the last position and the current position can be calculated with respect to position in the pre-operative three-dimensional model of the airway in order to help identify which branches have already been traversed. In this embodiment, the system may remember the history of all time points and positions of the optical shape sensing device.

As also described for the embodiment of FIG. 6, the pre-operative three-dimensional model is transformed to the new device location as a whole. Afterwards as the optical shape sensing device is advanced in the airways, the location is recorded at each time point and then used to deform the airway to fit the optical shape sensing device such as by keeping the optical shape sensing device at the center of the airway lumen. In the method of FIG. 6, the system stores the history of all device time points and positions as the interventional medical device is moved throughout the airways. These time points and positions may be important for devices where only the tip is tracked, or with minimal tracking along the length of the interventional medical device. The history of positions can be used to deform the model along the entire device trajectory and not just at the tip of the interventional medical device.

The embodiment of FIG. 6 is described using optical shape sensing devices. However, electromagnetic sensing devices can be used, either with a single sensor at the tip or multiple sensors along the length of the interventional medical device. For an electromagnetic sensor at the tip, recording of the tip position may take place continuously to track the path taken by the electromagnetic sensing device.

Figure 7:
FIG. 7 illustrates a virtual bronchoscopic view of the airways from a current position of a tracked device determined using dynamic interventional three-dimensional model deformation, in accordance with a representative embodiment.

FIG. 7 illustrates a bronchoscopic view of the airways from a current position of a tracked device determined using dynamic interventional three-dimensional model deformation, in accordance with a representative embodiment.

In FIG. 7, a bronchoscopic view is shown as a separate image from the image of the three-dimensional model. The tracked device is shown in the pathways of the three-dimensional model along with the path taken by the tracked device. Using methods as described in FIG. 4 and FIG. 6, the position of a tracked interventional medical device relative to the three-dimensional model of the anatomy can be determined. The bronchoscopic view can be created based on the position of the tip of the tracked interventional medical device, such as when the tracked interventional medical device is tracked with optical shape sensing. It may also be shown from any other fixed position on the medical device of interest.

A virtual bronchoscopic view may be formed from a segmented three-dimensional model based on the computed tomography data. The positional information of the tracked device can be used to determine the closest location of the tracked device to the planned path. Simply calculating the distance between the planned path and the current path and executing one or more error minimization routines, the position of the interventional medical device tip along the planned path can be determined. The bronchoscopic view at this position can then be shown to the user and automatically updated as the tracked device is moved throughout the airways.

The three-dimensional positional information of the tracked device relative to the three-dimensional model can be used to show a virtual bronchoscopic view of the insides of the airways.

For example, the three-dimensional model may be updated dynamically, and the tip of the tracked device can be shown with the deformed three-dimensional model. Alternatively, a path from the trachea to a target can be planned, and then the position of the tracked device can be compared to the planned path. Error minimization can be used to select the most appropriate location of the device tip to the planned path and to show the bronchoscopic view from this point in the three-dimensional model. As an example of a method implemented by a controller, a virtual bronchoscopic view can be created based on positions of a fixed point of the tracked device; determining closest locations of a planned path to the positions of the fixed point of the tracked device; and automatically updating the bronchoscopic view as the tracked device is moved through the three-dimensional model.

In an embodiment, an orientation of the tracked device can be identified and then used to determine a viewpoint for the virtual bronchoscopic view based on the orientation of the tracked device. For example, if a user wants to show the bronchoscopic view in front of the tip of the tracked device and show where the device tip will be moving to next, the orientation can be used to ensure the user is not viewing areas to the side or behind the tip. Similarly, knowing when to show a side view may also provide advantages for a user, such as when the tracked device tip gets close to a branch in the three-dimensional model. Proximity to a branch may be automatically used to trigger a display of multiple virtual bronchoscopic views to help the user move down the correct branch.

Figure 8:
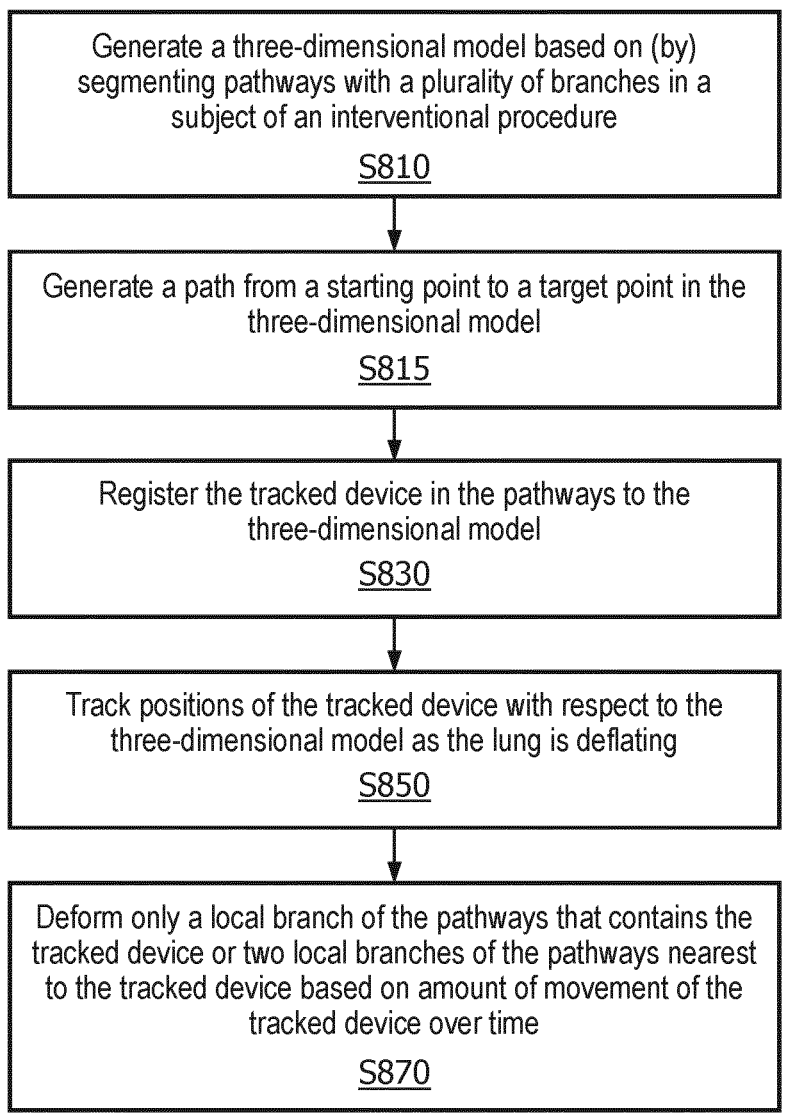
FIG. 8 illustrates another method of dynamic interventional three-dimensional model deformation, in accordance with a representative embodiment.

FIG. 8 illustrates another method of dynamic interventional three-dimensional model deformation, in accordance with a representative embodiment.

The method in FIG. 8 starts at S810 by generating a three-dimensional model based on segmenting pathways with multiple (a plurality of) branches in a subject of an interventional procedure.

At S815, the method in FIG. 8 includes generating a path from a starting point to a target point in the three-dimensional model.

At S830, the method in FIG. 8 includes registering the tracked device in the pathways to the three-dimensional model At S850, positions of the tracked device are tracked with respect to the three-dimensional model as a lung is deflating.

At S870, the method in FIG. 8 includes deforming only a local branch of the pathways that contains the tracked device or two local branches of the pathways nearest to the tracked device based on the amount of movement of the tracked device over time. For example, the amount of movement may be used as the basis for calculating an offset, and then the three-dimensional model may be corrected based on the offset.

The method in FIG. 8 overlaps in many key aspects the method in FIG. 4, but also diverges in several respects. For example, the method in FIG. 8 is particular to a medical intervention involving the lungs, and even involves tracking positions of the tracked device as the lung is deflating. Additionally, at S880 the deforming is limited to only one or two local branches though this is not prohibited at S480. Rather, as should be clear, features of various embodiments such as the embodiment of FIG. 8 may be exchanged with features in other embodiments, or added into other embodiments.

As described above, the method of FIG. 8 involves registering a deflated lung model and an inflated lung model using interventional medical device tracking. The optical shape sensing device (or another tracked device) is registered to the pre-operative three-dimensional model. Before surgery, the optical shape sensing device (or other tracked device) is navigated to the location of the target lesion (endobronchially). The navigating can be performed, for example, using the methods described above. The history of all device time points and positions is recorded with respect to the pre-operative model in order to identify which branches have been traversed and which lobe of the lung the optical shape sensing device is in. The lung is then deflated, and as the lung is deflated the position of the optical shape sensing device is tracked with respect to the pre-operative model. The pre-operative model is then deformed to the current position of the optical shape sensing device. The deforming could be local, such as deforming only the lobe containing the optical shape sensing device and the target lesion. Alternatively, in cases where the lesion sits between two lobes, both of the lobes could be deformed. The new deformed three-dimensional model is presented to the user representing the deflated lung state.

Figure 9:
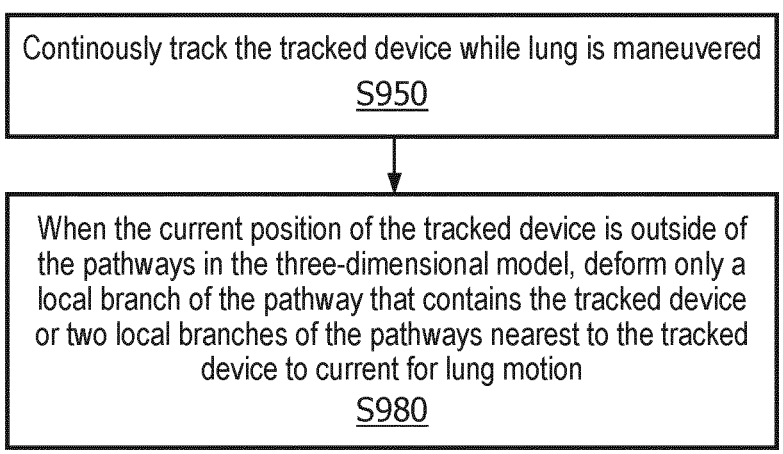
FIG. 9 illustrates another method of dynamic interventional three-dimensional model deformation, in accordance with a representative embodiment.

FIG. 9 illustrates another method of dynamic interventional three-dimensional model deformation, in accordance with a representative embodiment.

In FIG. 9, the process starts at S950 by continuously tracking the tracked device while the lung is maneuvered.

At S980, the process in FIG. 9 includes deforming only a local branch of the pathway that contains the tracked device or two local branches of the pathways nearest to the tracked device to correct for lung motion.

As described above, for the method in FIG. 9 lung motion can be tracked during a surgical resection using the deformation described herein. As with other embodiments, the embodiment of FIG. 9 involves registering the optical shape sensing device (or other tracking device) to the pre-operative model. The tracked device is navigated before the surgery to the location of the target lesion endobronchially.

During surgical dissection, the motion of the registered optical shape sensing device is tracked while the lung is maneuvered such as by being pulled, stretched or flipped by the surgeon. Based on the motion of the optical shape sensing device, the pre-operative model is deformed to the current position of the optical shape sensing device. The deformation may be local such as by deforming only the lobe containing the optical shape sensing device and the target lesion. Alternatively, in cases where the lesion sits between two lobes, both of the lobes can be deformed.

The methods of FIGS. 6, 8 and 9 have some degree of similarity, but describe three different use cases. The use case for FIG. 6 is moving an optical shape sensing tracked device from the trachea to a distal airway. The use case for FIG. 8 is keeping the optical shape sensing tracked device in one airway and collapsing the lung. The use case for FIG. 9 is keeping the optical shape sensing tracked device in one airway but physically moving the lung with a tool from the outside surface of the lung as is done in surgery.

An algorithm for the surgical method of FIG. 9 is described now and is also applicable to the embodiments of FIGS. 6 and 8. The following description details an algorithm using real data for implementing the surgical method of FIG. 9. Initially, a three-dimensional image of the anatomy of interest can be acquired pre-operatively or intra-operatively, and the three-dimensional anatomical image is segmented to form a mesh of the anatomy of interest such as airways. The three-dimensional mesh consists of a number of faces and vertices (i.e. points in a three-dimensional coordinate system). The coordinate systems of the optical shape sensing device and the imaging modality are registered so the x, y, z positions of the optical shape sensing device are in the same coordinate system as the x, y, z positions of the airway mesh. The position of the optical shape sensing device is continuously measured at this point in the workflow and the positional coordinates are sent to a computer processor.

For a sequence of frames starting at frame (n−1) the optical shape sensing device coordinates are stored. Tissue may be manipulated in many ways at this point, though no manipulation of tissue is specifically required here. At frame (n) the distance between the optical shape sensing device coordinates at frame (n) and at frame (n−1) is calculated. If the optical shape sensing device consists of multiple positional points, then the distance is calculated between each respective point along the optical shape sensing device. This offset between frames is then stored. For each point in the mesh, the distance between the mesh point(i) and the optical shape sensing device points (j:j+N) is calculated. The optical shape sensing device point closest to the mesh point(i) is determined via a distance minimization calculation. The previously calculated offset at this optical shape sensing device point is added to mesh point (i) and the new mesh point (i) coordinate is stored. This is repeated for all mesh points. After all mesh points are adjusted by the optical shape sensing device offset a new mesh can be displayed that has been dynamically deformed based on the optical shape sensing device position. This continuous process can be performed for all frames of optical shape sensing data (n:n+M)—resulting in a real-time mesh visualization.

The above implementation for the embodiment of FIG. 9 may also be applied to the embodiments of FIGS. 6 and 8 for device movement and deflating lung, respectively. However, the algorithms may be varied, such as by adding thresholds to distance calculations and offsets to exclude parts of the mesh from being deformed. For example, if the optical shape sensing device is in an airway on the right side of the lung, deformation of the left side of the lung may not be desired since information on how much that lung is moving may not be available. Additionally, it may be optimal to only deform the lobe of the lung in which the optical shape sensing device is present and not the other lobes of the same lung. Setting a threshold on the maximum amount of acceptable distance from the optical shape sensing device to the mesh point can restrict which mesh points are adjusted.

Additionally, the mesh is a three-dimensional volume of the anatomy. A centerline may be drawn within the mesh. A determination may be made as to whether the optical shape sensing device is within the mesh volume, or otherwise how far the mesh is off-center. The optical shape sensing device position can be compared to the mesh centerlines. Using an error minimization technique, the optical shape sensing device position with respect to the best matching location against the centerlines can be computed.

In an embodiment, a threshold may be implemented to determine if the optical shape sensing device is outside of the mesh volume. Fine adjustments may be made to the mesh to deform accordingly.

In another embodiment, the best matching location will determine which branch, lobe, or lung the optical shape sensing device is currently sitting in. This information may be used to also restrict which parts of the mesh are deformed versus those that are left undeformed.

In still another embodiment, the distance from the centerline may also be used to transform the mesh. For example, if the optical shape sensing device is only slightly offset from the centerline, the transform (or shift) necessary to re-center the optical shape sensing device with respect to the mesh can be computed so as to allow the optical shape sensing device to always "appear" at the center of the mesh.

In another embodiment, continuous saving of the optical shape sensing device position can be used to determine the current branch in which the optical shape sensing device is in. Determining which branch an optical shape sensing device is in using, for example best matching as described above, but the historical information is useful for reducing the computational processing time of determining the current branch. If the historical data says the optical shape sensing device is already in the left side of the lung, then the computation using the centerline described above can eliminate the right sided branches from the computation and only focus on the left sided branches.

The continuous saving of the device position may also be used for devices that do not use optical shape sensing or devices which only track one or a few select points. These coordinates may be saved for every frame of data to build a device track which can then be used in a similar manner to the implementations described above.

Figure 10:
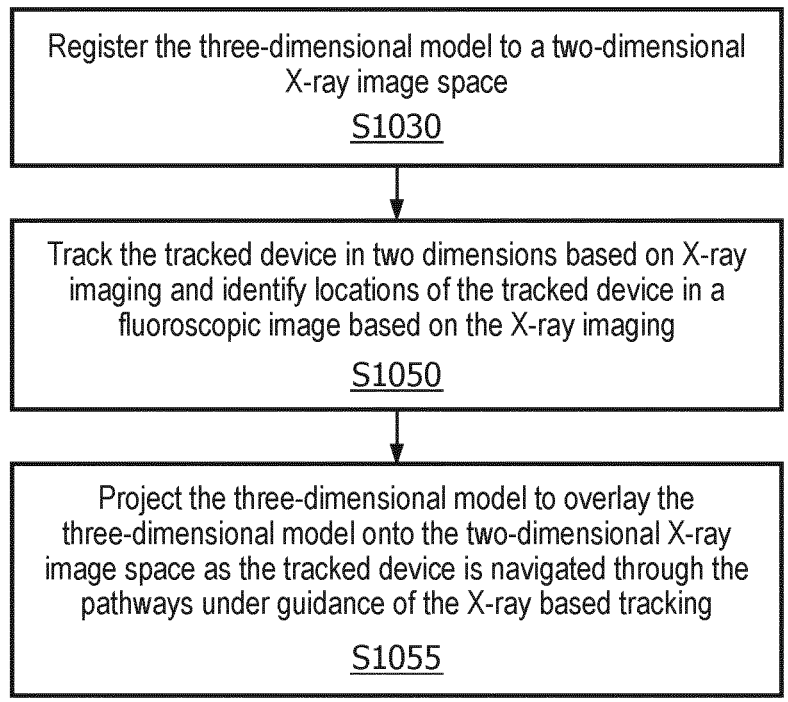
FIG. 10 illustrates another method of dynamic interventional three-dimensional model deformation, in accordance with a representative embodiment.

FIG. 10 illustrates another method of dynamic interventional three-dimensional model deformation, in accordance with a representative embodiment.

In FIG. 10, the process starts at S1030 by registering the three-dimensional model to a two-dimensional X-ray image space.

At S1050, the process in FIG. 10 continues by tracking the tracked device in two dimensions based on the X-ray imaging and identifying locations of the tracked device in a fluoroscopic image based on the X-ray imaging.

At S1055, the process in FIG. 10 includes projecting the three-dimensional model to overlay the three-dimensional model onto the two-dimensional X-ray image space as the tracked device is navigated through the pathways under guidance of the X-ray based tracking.

As described above, the method of FIG. 10 involves using X-ray based tracking of devices to identify the interventional medical device location in two-dimensional and adjusting the three-dimensional orientation and position of the three-dimensional segmented model. The method of FIG. 10 includes registering the three-dimensional segmented model to the two-dimensional x-ray image space such as by using fiducials, markers, or an isocenter. The three-dimensional segmented model is projected in two-dimensional to overlay the model on the x-ray image. Next, the tracked device is navigated down the airways under two-dimensional fluoroscopic guidance, and an image frame from the fluoroscopy is analyzed with image processing techniques to automatically identify the interventional medical device. The position of the tracked device can be extracted from the image and compared to the projection image of the three-dimensional model. The position of the tracked device can be checked to see if the tracked device is within the projected airway. Alternatively, the distance between the interventional medical device position and a centerline of the projected airway can be calculated with a threshold set to define whether the interventional medical device is within the airway or not The method of FIG. 10 can be modified to apply to segmentation of vessels instead of airways. The distance between the interventional medical device position and a centerline of the projected vessel can again be calculated. Similarly, the method of FIG. 10 can be adjusted so that the projected model of the airway can be deformed to fit the actual device position if the interventional medical device is found to be outside of the actual airway or vessel. An out of plane component of the motion in the two-dimensional X-ray image can be accounted for using a small fiducial, as this may be challenging using only three-dimensional projections. Additionally, the x-ray image may be acquired from alternative angles to occasionally adjust the out-of-plane information.

Additionally, although not shown in FIG. 2, a tracked device 250 may be tracked with the assistance of a hub such as when the tracked device 250 is being registered using fluoroscopic imaging as in FIG. 10. An alternative method for registering the tracked device to fluoroscopy is described as follows: A hub as described herein may be placed in the trachea. The hub may contain a path of a known pattern. As the tracked device 250 is guided through the hub, the trajectory of the tracked device 250 is examined for this special path. Once the special hub path is found in the device trajectory, it can be used to register the tracked device 250 to the hub. Then, a fluoroscopic image can be used to register the hub with respect to fluoroscopy; the hub may contain radiopaque markers or other discernable features, which are conducive to localizing the hub with respect to the fluoroscopic image. This allows the hub and fluoroscopy to be registered to each other. In combining these to sub-registrations, a full registration between the tracked device 250 and fluoroscopy is achieved.

Figure 11:
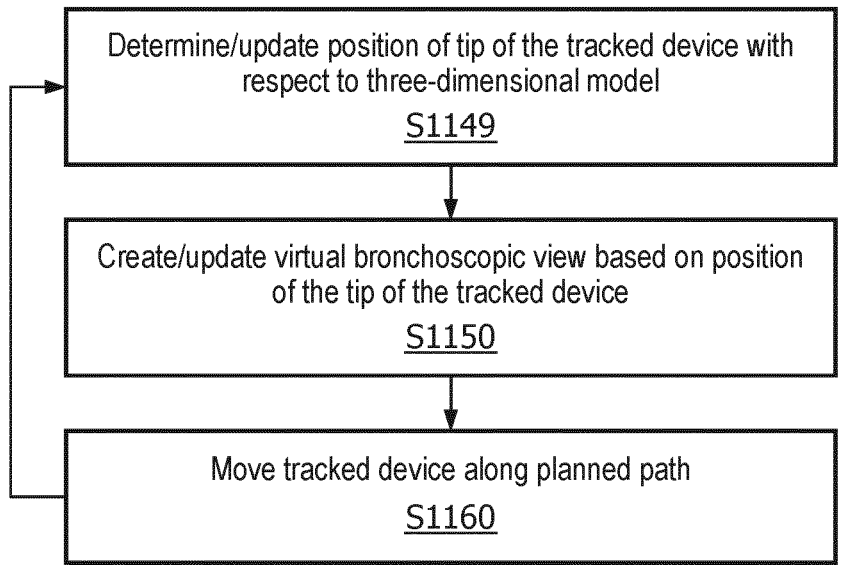
FIG. 11 illustrates another method of dynamic interventional three-dimensional model deformation, in accordance with a representative embodiment.

FIG. 11 illustrates another method of dynamic interventional three-dimensional model deformation, in accordance with a representative embodiment.

In FIG. 11, the process starts at S1149 by determining a position of the tip of the tracked device with respect to (relative to) the three-dimensional model. At S1150, the process continues by creating a virtual bronchoscopic view based on the position of the tip of the tracked device.

At S1160, the tracked device is moved along the planned path, and the process returns to S1149 and S1150 to update the position of the tip and the virtual bronchoscopic view.

The method of FIG. 11 may involve showing a bronchoscopic view of an interventional medical device tip using an optical shape sensing position. In the method of FIG. 11, the position of the interventional medical device is determined relative to the anatomical model, and the bronchoscopic view can be created based on the position of the interventional medical device tip. The positional information of the interventional medical device at positions of a fixed point of the tracked device can be used to determine the closest location of a planned path. Simply calculating the distance between the planned path and the current path and performing error minimization routines, the position of the interventional medical device tip along the planned path can be determined. The bronchoscopic view at this position can then be shown to the user and automatically updated as the interventional medical device is moved throughout the airways. For example, a method implemented by a controller may include creating a virtual bronchoscopic view based on each of multiple positions of a fixed point of the tracked device; determining closest locations of a planned path to the positions of the fixed point of the tracked device; and automatically updating the bronchoscopic view as the tracked device is moved through the three-dimensional model. The fixed point of the tracked device may be the tip of the tracked device.

An example of the bronchoscopic view of the airways at a point marked on a three-dimensional pre-operative model as acquired in FIG. 11 is shown in FIG. 7. Anatomical features are shown in FIG. 7 beyond just the lumen. The method of FIG. 11 can provide additional imaging views of what is directly outside the airway walls to provide better guidance for when to exit the airways. For example, the imaging of what is outside the airway walls can assist an interventionist by providing visual guidance not to exit when there is a large blood vessel directly outside of the airway wall.

Figure 12:
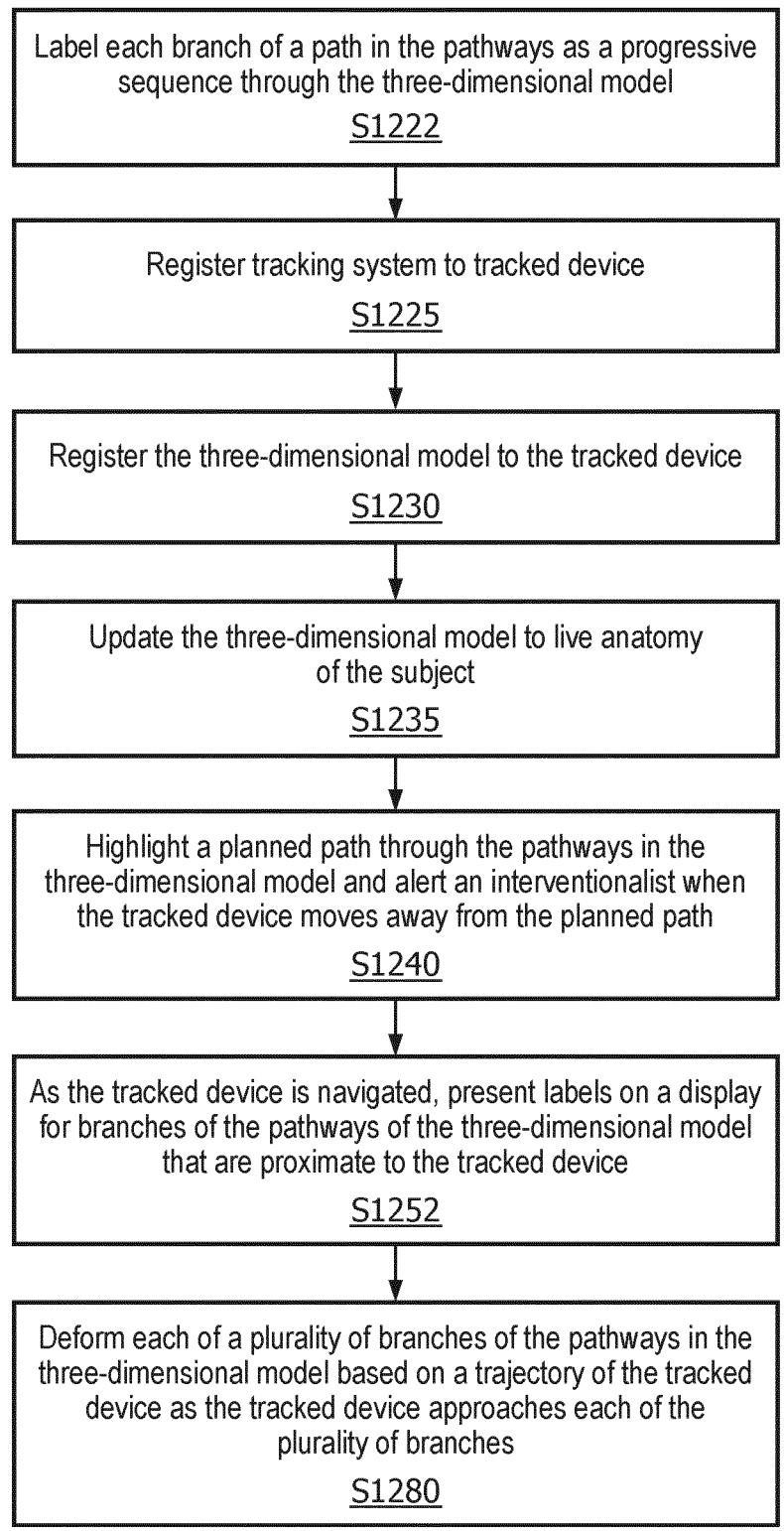
FIG. 12 illustrates another method of dynamic interventional three-dimensional model deformation, in accordance with a representative embodiment.

FIG. 12 illustrates another method of dynamic interventional three-dimensional model deformation, in accordance with a representative embodiment.

In FIG. 12, the process starts at S1222 by labelling each branch of a path in the pathways as a progressive sequence through the three-dimensional model.

At S1225, the tracking system (e.g., optical shape sensing) is registered to the tracked device in order to track the tracked device. This registration may be inherent in the mechanical integration of the tracking to the tracked device, such as the tracking element being fixed to the distal tip of the tracked device. In the case of shape sensing, a hub can be fixed to the tracked device in a predetermined manner, which then allows the shape sensing fiber to be registered to the tracked device. However, position tracking in FIG. 12 is not limited to optical shape sensing, and other forms of position tracking such as sensors may also or alternatively be used.

At S1230, the three-dimensional model is registered to the tracked device.

At S1235, the process in FIG. 12 includes updating the three-dimensional model to live anatomy of the subject.

At S1240, the process in FIG. 12 includes highlighting a planned path through the pathways in the three-dimensional model and alerting an interventionalist when the tracked device moves away from the planned path.

At S1252, the process in FIG. 12 includes presenting labels on a display for branches of the pathways of the three-dimensional model that are proximate to the tracked device as the tracked device is navigated.

At S1280, the process in FIG. 12 includes deforming each of multiple (a plurality of) branches of the pathways in the three-dimensional model based on a trajectory of the tracked device as the tracked device approaches each of the multiple (plurality of) branches.

In the method of FIG. 12, the airways are first segmented and planned paths created as described above. In addition, each branch in the model of the airway is distinctly labelled. An intuitive labelling scheme may be hierarchical and/or based on clinical nomenclature. The net effect is that a planned path can be communicated in terms of a sequence of branches, in addition to a visually continuous course. The method of FIG. 12 may be based on an assumption that the bronchoscope has a shape sensing fiber, or another position tracking mechanism embedded within so that the bronchoscope is fully tracked, or that a shape-sensed device is provided through the working channel of the bronchoscope, or that a shape-sensed device is provided through the working channel and a hub is used to track the non-shape-sensed bronchoscope. A working hub may be used in the embodiment where optical shape sensing fibers are used but is not necessarily required.

Additionally, in the method of FIG. 12 the model of the airway is registered to the shape-sensed device, bronchoscope image and/or fluoroscopy, which allows the system to transfer the branch labels from the computed tomography to the images later in the procedure. Breathing motion as well as patient motion are tracked via optical shape sensing or another position tracking mechanism as long as the interventional medical device is in an airway. Since the upper airways are relatively rigid, the upper airways deform less due to physiological motion. The model of the airway can be updated to the live anatomy by initializing the position and orientation of the model against the upper airways seen in a fluoroscopic image, then following the tracked breathing/patient motion to update continuously. To further assist registration in the case of an optical shape sensing device or another position tracking device, a small device that operates similarly to a dynamic hub may be placed in the trachea to provide a reference in the body regarding the location of the bronchoscope.

Using the model of the airway and labelling, the operator involved in the method of FIG. 12 navigates the bronchoscope to the next branch on the planned path. During navigation, branch labels appear in the bronchoscope image as the bronchoscope approaches the branches, or in the virtual bronchoscope image if the shape-sensed device is navigated through the working channel and deep into the airways beyond the bronchoscope itself. This may indicate to the user that a navigation decision must soon be made, and which branch the user should guide the bronchoscope or optical shape sensing device (or other position tracking device) towards.

As the user navigates the bronchoscope or optical shape sensing device (or other position tracking device) through the branch in FIG. 12, the system detects that the branch has been traversed, and which branch has been taken. This determination is possible because the computed tomography and segmented airways are registered to the shape-sensed bronchoscope or device. This particular segment of the model of the airway is deformed based on the interventional medical device trajectory. Note that the locations of branch labels update to the deformed model. Furthermore, deformation is anchored by upper airway locations which deform less and by locations of the branches taken. Distal segments of the airway that the device has not yet reached may be rigidly coupled to the newly deformed airway segments as an approximation, in order to maintain a sensible visualization of the remaining airways to the user. If the correct branch is taken based on the desired planned path, the path is highlighted to indicate the successful branch taken. Otherwise an alert is provided. As navigation proceeds, airways unrelated to the current path may be progressively deemphasized visually while still remaining visible to provide overall context. Additionally, each traversed branch can be labelled in the fluoroscopic image, so that the user can see the paths/branches traversed in the live image.

The above sequence of branch traversal and path highlighting proceeds until the target is reached. The net effects of the approach in FIG. 12 is that deformation of the model only needs to address the planned path and paths taken, as opposed to the entire model, which removes visual clutter and is simpler to implement; the user retains greater confidence in navigating down the correct path even in the presence of registration uncertainty and imperfect deformation of the models; and can improve the accuracy of the registration based on the bronchoscopy image and knowing if the bronchoscope is in the center of the lumen or closer to the wall.

Moreover, even without tracking, the bronchoscope in FIG. 12 could be registered to the pre-operative segmentation model based only on the positions/orientations of the branches in the bronchoscope view.

A hybrid approach to register the three-dimensional model to the anatomy intraoperatively is also possible, such as to provide navigation before registration. As the tracked bronchoscope is guided down the trachea, when there is not yet enough information in the tracking system to register the model to the anatomy, bronchoscopy images can be analyzed in real time to estimate the path and pose of the bronchoscope. Branches seen in the bronchoscope images can then be used to refine the registration further. This provides a reasonable early estimate of the bronchoscope trajectory, particularly in the rigid upper airways. Then, as branches are taken, the registration is refined using the tracking and information of the branches and paths taken.

In one or more embodiments alternative to those described already, the pre-operative three-dimensional models may remain static and the tracked interventional medical device may instead be deformed based on tracheal reference, paths traversed, branches taken, etc.

Figure 13:
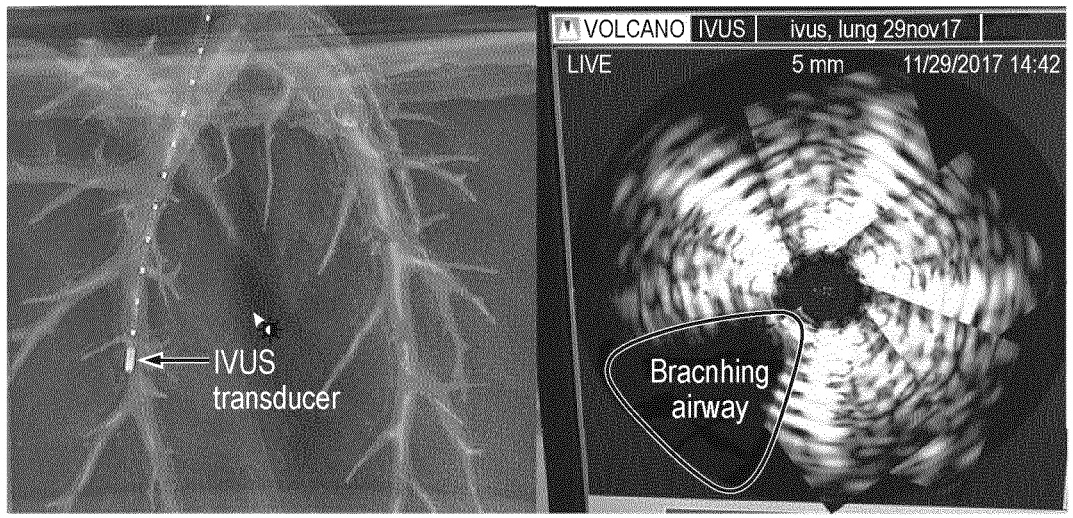
FIG. 13 illustrates an intraluminal view of airways from a current position of a tracked device determined using dynamic interventional three-dimensional model deformation, in accordance with a representative embodiment

FIG. 13 illustrates an intraluminal view of airways from a current position of a tracked device determined using dynamic interventional three-dimensional model deformation, in accordance with a representative embodiment.

In FIG. 13, a radial endobronchial ultrasound (REBUS) catheter is navigated down the right main branch and into small peripheral airways. The ultrasound transducer produces a radial image of the airway in which the ultrasound transducer is sitting. When there is contact with the wall of the airway the image appears white and when there is a branching airway the image appears black because all signal is lost to the air in that location.

In the embodiment of FIG. 13, the REBUS catheter is tracked with ultrasound imaging information as a pseudo-tracking mechanism rather than with optical shape sensing.

However, in an embodiment based on FIG. 13, a REBUS catheter is tracked with optical shape sensing along with the ultrasound imaging information.

Figure 14:
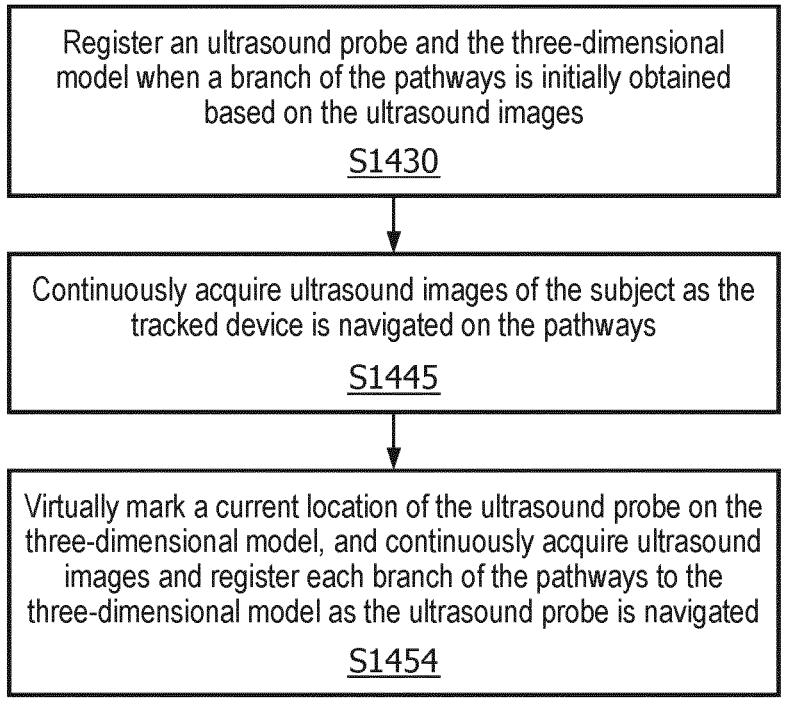
FIG. 14 illustrates another method of dynamic interventional three-dimensional model deformation, in accordance with a representative embodiment.

FIG. 14 illustrates another method of dynamic interventional three-dimensional model deformation, in accordance with a representative embodiment.

In FIG. 14, the process starts at S1430 by registering an ultrasound probe and the three-dimensional model when a branch of the pathways is initially obtained based on the ultrasound images.

At S1445, the process of FIG. 14 includes continuously acquiring ultrasound images of the subject as the tracked device is navigated on the pathways.

At S1454, the process of FIG. 14 includes virtually marking a current location of the ultrasound probe on the three-dimensional model, and continuously acquiring ultrasound images and registering each branch of the pathways to the three-dimensional model as the ultrasound probe is navigated. For example, diameter of the airways may be compared to the three-dimensional model to provide a rough context of which branch the tracked device is in. Additionally, in the embodiment of FIG. 14, ultrasound itself is the tracking method. However, an interventional tool such as an ultrasound catheter may also be tracked with another type of tracking technology such as optical shape sensing or electromagnetics.

In the method of FIG. 14 described above, radial endobronchial ultrasound (REBUS) is used to assess the airways and guide needle biopsies and to guide navigation and determine the location of the transducer with respect to the three-dimensional segmented model. A method for using (R)EBUS guided and tracked navigation is described in part by FIG. 14. The (R)EBUS probe is navigated in the left or right main branch, and ultrasound imaging is continuously acquired from the (R)EBUS probe. Ultrasound imaging as in FIG. 14 may assume is good image quality and no air pocket between the transducer and the airway wall. When the first branch is seen in the ultrasound image an initial registration between the probe and the three-dimensional segmented model is established. A first branch is shown in FIG. 13 as a dark gap. A virtual marker may be placed on the three-dimensional model to indicate the current location of the transducer. As the probe is navigated further into the airways, ultrasound images are continuously acquired, and each branch is registered to the pre-operative computed tomography or to the segmented three-dimensional model. Additionally, every time a branch is visualized the virtual marker position is updated on the three-dimensional model; and if no branch is within the ultrasound image the virtual marker position can be estimated with some indication as to the uncertainty of the location.

Automatic labeling described in previous embodiments can be combined with the embodiment of FIG. 14. For example, diameter and wall thickness of the airway that the EBUS transducer is currently sitting in can be calculated and referenced back to the three-dimensional model. The three-dimensional model, generated from the three-dimensional imaging, may also include information about the airway diameter and airway wall thickness at all positions. Registering this information between the REBUS probe and the three-dimensional model determines an approximate position of the transducer. Adding in additional information about which branches have been passed through can be used to determine the exact location of the transducer. Additionally, while the description of FIG. 14 and most embodiments herein focuses on airways, methods such as in FIG. 14 including the updated method using automatic labelling can also be used in vascular navigation.

A method implemented by a controller may include automatically determining the position of a tip of an ultrasound probe that is used to acquire the ultrasound images by calculating a diameter and wall thickness of a pathway from the ultrasound images and comparing the diameter and wall thickness to the three-dimensional model. The controller may also optimize the position of the tip of the ultrasound probe based on previous locations of the ultrasound probe.

In FIG. 14, the location and orientation of the transducer can be further refined by measuring the diameter of the branching airway and the orientation of the airway with respect to the transducer in the image. Keeping track of each branch that the transducer passes can provide a better assessment as to which branch and path the entire device has gone down. A virtual image of the entire (R)EBUS probe can then be shown on the three-dimensional segmented model.

Additionally, in FIG. 14 a virtual three-dimensional ultrasound image or roadmap of the airways may be constructed based on the tracked (R)EBUS. This may be shown on the pre-operative segmentation model. Furthermore, the pre-operative model may be updated to match the virtual (R)EBUS roadmap, e.g. based on deformable correction techniques described earlier.

Intermittent x-ray images can also be used to update the location of the virtual marker or check virtual device positioning consistent with the embodiment in FIG. 14. Similarly, tracking such as optical shape sensing may be incorporated with the ultrasound-based approach to reduce the uncertainty, particularly in branch locations where image quality is reduced.

Accordingly, dynamic interventional three-dimensional model deformation enables dynamic navigational correction during interventional procedures. The dynamic interventional three-dimensional model deformation is applicable to multiple different imaging modes such as X-ray and ultrasound, and to multiple different organs of a human subject including the lungs as well as the vascular system. Dynamic interventional three-dimensional model deformation may be added as functionality to an existing product such as a device tracking product. The primary application discussed for lung biopsy is not an absolute requirement, as dynamic interventional three-dimensional model deformation may also be used for other pulmonology applications such as surgical excision or ablating tissue. Additionally, dynamic interventional three-dimensional model deformation may be applied to other fields such as vascular or gastrointestinal. Additionally, dynamic interventional three-dimensional model deformation applies to both Rayleigh (enhanced and regular) as well as Fiber Bragg implementations of shape sensing fiber, as well as both manual and robotic manipulation of such devices. Finally, dynamic interventional three-dimensional model deformation applies to both X-ray based tracking of devices and ultrasound tracking of devices, in additional to optical shape sensing implementations.

Although dynamic interventional three-dimensional model deformation has been described with reference to several exemplary embodiments, it is understood that the words that have been used are words of description and illustration, rather than words of limitation. Changes may be made within the purview of the appended claims, as presently stated and as amended, without departing from the scope and spirit of dynamic interventional three-dimensional model deformation enables in its aspects. Although dynamic interventional three-dimensional model deformation enables has been described with reference to particular means, materials and embodiments, dynamic interventional three-dimensional model deformation enables is not intended to be limited to the particulars disclosed; rather dynamic interventional three-dimensional model deformation enables extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A controller for assisting navigation in an interventional procedure, comprising:
a memory that stores instructions, and
a processor that executes the instructions,
wherein, when executed by the processor, the instructions cause the controller to implement a process that includes:
obtaining a three-dimensional model generated prior to an interventional procedure based on segmenting pathways with a plurality of branches in a subject of the interventional procedure;
receiving current positional information from an optical shape sensing of a tracked device, wherein the tracked device is tracked using this optical shape sensing;
determining, during the interventional procedure, whether a current positional information of the tracked device is outside of the pathways in the three-dimensional model;
when the current positional information of the tracked device is outside of the pathways in the three-dimensional model, deforming the three-dimensional model to the current
positional information of the tracked device; and
highlighting a planned path through the pathways in the three-dimensional model and alerting a user when the tracked device moves away from the planned path.

2. A controller for assisting navigation in an interventional procedure, comprising:
a memory that stores instructions, and
a processor that executes the instructions,
wherein, when executed by the processor, the instructions cause the controller to implement a process that includes:
obtaining a three-dimensional model generated prior to an interventional procedure based on segmenting pathways with a plurality of branches in a subject of the interventional procedure; receiving current positional information from an optical shape sensing of a tracked device, wherein the tracked device is tracked using this optical shape sensing;
determining, during the interventional procedure, whether a current positional information of the tracked device is outside of the pathways in the three-dimensional model; and
when the current positional information of the tracked device is outside of the pathways in the three-dimensional model, deforming the three-dimensional model to the current positional information of the tracked device;
wherein the process implemented when the processor executes the instructions further comprises:
registering the tracked device in the pathways to the three-dimensional model;
calculating an offset between an immediately previous positional information of the tracked device and the current positional information of the tracked device relative to the
three-dimensional model;
transforming the three-dimensional model to the current positional information of the tracked device based on the offset, and
iteratively locally deforming each new branch of the three-dimensional model containing the tracked device each time the tracked device moves to a new branch.

3. The controller of claim 2, wherein the process implemented when the processor executes the instructions further comprises:

tracking the tracked device in two dimensions based on X-ray imaging; and registering the three-dimensional model to a two-dimensional X-ray image space.

4. The controller of claim 3, wherein the process implemented when the processor executes the instructions further comprises:

projecting the three-dimensional model to overlay the three-dimensional model onto the two-dimensional X-ray image space as the tracked device is navigated through the pathways under guidance of the tracking based on X-ray imaging; and identifying locations of the tracked device in a fluoroscopic image based on the X-ray imaging.

5. The controller of claim 2, wherein the process implemented when the processor executes the instructions further comprises:

creating a virtual bronchoscopic view based on positions of a fixed point of the tracked device;

determining closest locations of a planned path to the positions of the fixed point of the tracked device; and automatically updating the bronchoscopic view as the tracked device is moved through the three-dimensional model.

6. The controller of claim 2, wherein the three-dimensional model has been segmented to form a mesh of the subject in a coordinate system, wherein the optical shape sensing of the tracked device is registered in said coordinate system, said process further comprises for each point (i) of the mesh:

a) calculating the distance between the mesh point (i) and optical shape sensing device points (j:j+N) sensed along the optical shape sensing of the tracked device;

b) determining the one of said optical shape sensing device points (j:j+N) closest to the mesh point (i) via a distance minimization calculation;

c) adding said calculated offset of this optical shape sensing device point to mesh point (i);

d) storing the new mesh point (i) coordinate;

e) repeating (a) to (d) for all mesh points to get finally said deformed three- dimensional model.

7. A controller for assisting navigation in an interventional procedure, comprising:

a memory that stores instructions, and a processor that executes the instructions, wherein, when executed by the processor, the instructions cause the controller to implement a process that includes;

obtaining a three-dimensional model generated prior to an interventional procedure based on segmenting pathways with a plurality of branches in a subject of the interventional procedure; receiving current positional information from an optical shape sensing of a tracked device, wherein the tracked device is tracked using this optical shape sensing;

determining, during the interventional procedure, whether a current positional information of the tracked device is outside of the pathways in the three-dimensional model; and when the current positional information of the tracked device is outside of the pathways in the three-dimensional model, deforming the three-dimensional model to the current positional information of the tracked device, wherein the process implemented when the processor executes the instructions further comprises:

registering the tracked device in the pathways to the three-dimensional model; and when the current positional information of the tracked device is outside of the pathways in the three-dimensional model, the deforming the three-dimensional model comprises deforming only a local branch of the pathways that contains the tracked device or two local branches of the pathways nearest to the tracked device, wherein the pathways are through a lung, a vascular system or a gastro-intestinal system and the tracked device is navigated to a location in the lung, vascular system or gastro-intestinal system, prior to the interventional procedure.

8. A controller for assisting navigation in an interventional procedure, comprising:

a memory that stores instructions, and a processor that executes the instructions wherein, when executed by the processor, the instructions cause the controller to implement a process that includes:

obtaining a three-dimensional model generated prior to an interventional procedure based on segmenting pathways with a plurality of branches in a subject of the interventional procedure; receiving current positional information from an optical shape sensing of a tracked device, wherein the tracked device is tracked using this optical shape sensing;

determining, during the interventional procedure, whether a current positional information of the tracked device is outside of the pathways in the three-dimensional model; and when the current positional information of the tracked device is outside of the pathways in the three-dimensional model, deforming the three-dimensional model to the current positional information of the tracked device, wherein the process implemented when the processor executes the instructions further comprises:

when the current positional information of the tracked device is outside of the pathways in the three-dimensional model, the deforming of the three-dimensional model comprises deforming only a local branch of the pathways that contains the tracked device or two local branches of the pathways nearest to the tracked device, wherein the pathways are through a lung, a vascular system or a gastro-intestinal system;

deforming the three-dimensional model to the current positional information of the tracked device to correct for lung, vascular system or gastro-intestinal system motion or a lung, vascular system or a gastro-intestinal system deformation, and continuously tracking the tracked device while the lung, the vascular system or the gastro- intestinal system is maneuvered.

9. A controller for assisting navigation in an interventional procedure, comprising:

a memory that stores instructions, and a processor that executes the instructions, wherein, when executed by the processor, the instructions cause the controller to implement a process that includes:

obtaining a three-dimensional model generated prior to an interventional procedure based on segmenting pathways with a plurality of branches in a subject of the interventional procedure; receiving current positional information from an optical shape sensing of a tracked device, wherein the tracked device is tracked using this optical shape sensing;

determining, during the interventional procedure, whether a current positional information of the tracked device is outside of the pathways in the three-dimensional model; and when the current positional information of the tracked device is outside of the pathways in the three-dimensional model, deforming the three-dimensional model to the current positional information of the tracked device, wherein the process implemented when the processor executes the instructions further comprises:

labelling each branch of a path in the pathways as a progressive sequence through the three-dimensional model;

registering the three-dimensional model to the tracked device;

updating the three-dimensional model to live anatomy of the subject; and as the tracked device is navigated, presenting labels on a display for branches of the pathways of the three-dimensional model that are proximate to the tracked device.

10. A controller for assisting navigation in an interventional procedure, comprising:

a memory that stores instructions, and a processor that executes the instructions, wherein, when executed by the processor, the instructions cause the controller to implement a process that includes:

obtaining a three-dimensional model generated prior to an interventional procedure based on segmenting pathways with a plurality of branches in a subject of the interventional procedure; receiving current positional information from an optical shape sensing of a tracked device, wherein the tracked device is tracked using this optical shape sensing;

determining, during the interventional procedure, whether a current positional information of the tracked device is outside of the pathways in the three-dimensional model; and when the current positional information of the tracked device is outside of the pathways in the three-dimensional model, deforming the three-dimensional model to the current positional information of the tracked device, wherein the process implemented when the processor executes the instructions further comprises:

deforming each of a plurality of branches of the pathways in the three-dimensional model based on a trajectory of the tracked device as the tracked device approaches each of the plurality of branches.

11. A controller for assisting navigation in an interventional procedure, comprising:

a memory that stores instructions, and a processor that executes the instructions, wherein, when executed by the processor, the instructions cause the controller to implement a process that includes:

obtaining a three-dimensional model generated prior to an interventional procedure based on segmenting pathways with a plurality of branches in a subject of the interventional procedure; receiving current positional information from an optical shape sensing of a tracked device, wherein the tracked device is tracked using this optical shape sensing;

determining, during the interventional procedure, whether a current positional information of the tracked device is outside of the pathways in the three-dimensional model; and when the current positional information of the tracked device is outside of the pathways in the three-dimensional model, deforming the three-dimensional model to the current positional information of the tracked device, wherein the process implemented when the processor executes the instructions further comprises:

continuously acquiring ultrasound images of the pathways as the tracked device is navigated on the pathways;

registering an ultrasound probe and the three-dimensional model when a branch of the pathways is initially obtained based on the ultrasound images;

virtually marking a current location of the ultrasound probe on the three-dimensional model, and continuously acquiring ultrasound images and registering each branch of the pathways to the three-dimensional model as the ultrasound probe is navigated.

12. A controller for assisting navigation in an interventional procedure, comprising:

a memory that stores instructions, and a processor that executes the instructions, wherein, when executed by the processor, the instructions cause the controller to implement a process that includes:

obtaining a three-dimensional model generated prior to an interventional procedure based on segmenting pathways with a plurality of branches in a subject of the interventional procedure; receiving current positional information from an optical shape sensing of a tracked device, wherein the tracked device is tracked using this optical shape sensing;

determining, during the interventional procedure, whether a current positional information of the tracked device is outside of the pathways in the three-dimensional model; and when the current positional information of the tracked device is outside of the pathways in the three-dimensional model, deforming the three-dimensional model to the current positional information of the tracked device, wherein the process implemented when the processor executes the instructions further comprises:

continuously acquiring ultrasound images of the pathways as the tracked device is navigated on the pathways; and virtually marking the three-dimensional model each time a branch of the pathways is visualized.

13. The controller of claim 12, wherein the process implemented when the processor executes the instructions further comprises:

automatically determining the position of a tip of an ultrasound probe used to acquire the ultrasound images by calculating a diameter and wall thickness of a pathway from the ultrasound images and comparing the diameter and wall thickness to the three-dimensional model; and optimizing the position of the tip of the ultrasound probe based on previous locations of the ultrasound probe.

* * * * *